US011546569B2

(12) United States Patent
Sela

(10) Patent No.: US 11,546,569 B2
(45) Date of Patent: Jan. 3, 2023

(54) SYSTEM AND METHODS FOR CORRECTING IMAGE DATA OF DISTINCT IMAGES AND GENERATING AND STEREOSCOPIC THREE-DIMENSIONAL IMAGES

(71) Applicant: SYNAPTIVE MEDICAL INC., Toronto (CA)

(72) Inventor: Gal Sela, Toronto (CA)

(73) Assignee: Synaptive Medical Inc.

( * ) Notice: Subject to any disclaimer, the term of this patent is extended or adjusted under 35 U.S.C. 154(b) by 0 days.

(21) Appl. No.: 17/303,532

(22) Filed: Jun. 1, 2021

(65) Prior Publication Data

US 2021/0289189 A1 Sep. 16, 2021

Related U.S. Application Data

(63) Continuation-in-part of application No. 17/038,158, filed on Sep. 30, 2020, now Pat. No. 11,070,787, which is a continuation-in-part of application No. 16/384,075, filed on Apr. 15, 2019, now Pat. No. 10,827,162.

(51) Int. Cl.
*H04N 13/128* (2018.01)
*H04N 13/239* (2018.01)
*G06T 3/60* (2006.01)
*G06T 5/00* (2006.01)
*G06T 7/80* (2017.01)

(52) U.S. Cl.
CPC .......... *H04N 13/128* (2018.05); *G06T 3/608* (2013.01); *G06T 5/006* (2013.01); *G06T 7/85* (2017.01); *H04N 13/239* (2018.05); *G06T 2207/10028* (2013.01)

(58) Field of Classification Search
None
See application file for complete search history.

(56) References Cited

U.S. PATENT DOCUMENTS

2015/0109427 A1* 4/2015 Wood .................... A61B 34/10
348/68
2015/0296149 A1* 10/2015 Laroia .................. G02B 17/008
348/239
2018/0124380 A1* 5/2018 Berthilsson ............... G06T 7/74

* cited by examiner

*Primary Examiner* — Eileen M Adams

(57) ABSTRACT

An optical imaging system for imaging a target during a medical procedure, the optical imaging system involving a first camera for capturing a first image of the target, a second wide-field camera for capturing a second image of the target, at least one optional path folding mirror disposed in an optical path between the target and a lens of the second camera, and a processor for receiving the first image and the second image, the processor configured to apply an image transform to one of the first image and the second wide-field image and combine the transformed image with the other one of the images to produce a stereoscopic image of the target.

18 Claims, 14 Drawing Sheets

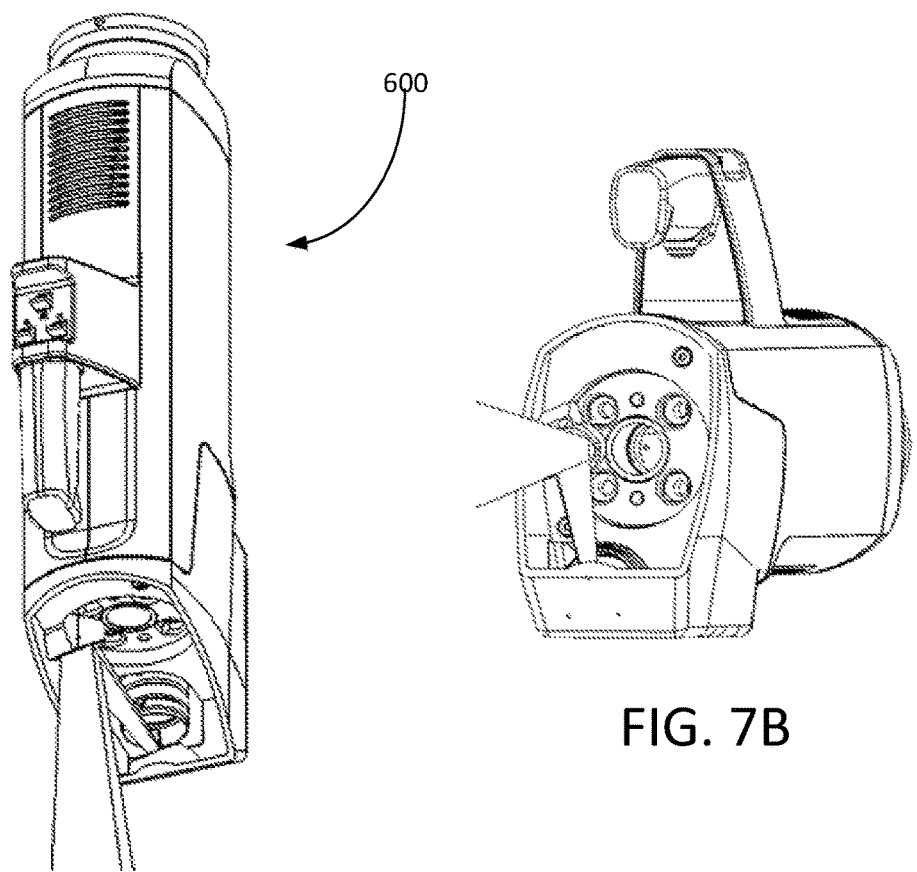
FIG. 7A
FIG. 7B
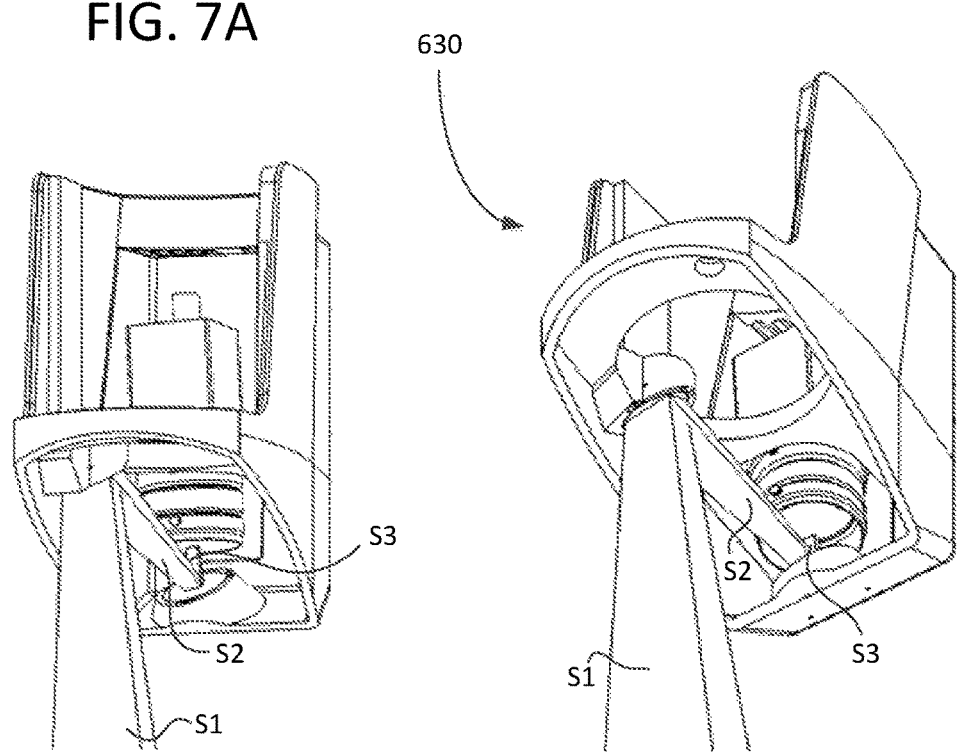
FIG. 7C
FIG. 7D

ES AND METHODS FOR
CORRECTING IMAGE DATA OF DISTINCT
IMAGES AND GENERATING AND
STEREOSCOPIC THREE-DIMENSIONAL
IMAGES

CROSS-REFERENCE TO RELATED APPLICATION(S)

This document is a continuation-in-part application which claims the benefit of, and priority to: (a) U.S. patent application Ser. No. 17/038,158, filed on Sep. 30, 2020, entitled "AUGMENTED OPTICAL IMAGING SYSTEM FOR USE IN MEDICAL PROCEDURES," and (b) U.S. patent application Ser. No. 16/384,075, filed on Apr. 15, 2019, entitled "AUGMENTED OPTICAL IMAGING SYSTEM FOR USE IN MEDICAL PROCEDURES," now U.S. Pat. No. 10,827,162, issued on Nov. 3, 2020, all of which are incorporated herein by reference in their entirety.

FIELD

The present disclosure relates to medical imaging, image processing, and, in particular, to optical imaging systems with image processing suitable for use in image-guided medical procedures.

BACKGROUND

Related art digital microscopes support advanced visualization during medical procedures. For example, digital surgical microscopes provide magnified views of anatomical structures during a surgery. Digital microscopes use optics and digital, e.g., charge-coupled device- (CCD-) based cameras, to capture images, in real-time, and output the images to displays for viewing by a surgeon, operator, etc.

In the related art, when producing a stereo three-dimensional (3D) video image, separate cameras are typically employed, corresponding to views from a left perspective and a right perspective. Traditionally, these cameras need to have identical optical properties such that the left perspective and the right perspective match. However, to allow for dynamic zoom and focus, maintaining this correspondence involves complex electro-mechanical linkages between a left optical chain and a right eye optical chain. Moreover, adding a second camera to an existing two-dimensional (2D) system is almost impossible without significant interconnections between the left optical chain and the right eye optical chain.

In related art image-guided medical applications, such as surgery or diagnostic imaging, accurate three-dimensional (3D) visualization of patient anatomy and surgical tools is crucial. Thus, a need exists for a lightweight digital microscope solutions that support accurate 3D visualization to overcome at least the foregoing related art challenges.

SUMMARY

In addressing at least many of the challenges experienced in the related art, the subject matter of the present disclosure involves a system and methods for generating and correcting a plurality of distinct images. Generally, correcting image data of the plurality of distinct images involves dynamically adjusting at least one optical property of each distinct set of optical properties of each distinct optical chain in relation to at least one optical property of another distinct set of optical properties of another distinct optical chain, in accordance with some embodiments of the present disclosure. Dynamically adjusting the at least one optical property comprises at least one of dynamically adjusting at least one physical parameter of each distinct set of physical parameter of each distinct optical chain and dynamically adjusting output data, such as, but not limited to, image data, of each distinct optical chain. Dynamically adjusting output data comprises at least one of manipulating and transforming the output data by applying at least one image processing technique thereto. Applying the at least one image processing technique comprises warping pixel locations of at least one image as well as any other image processing technique.

In accordance with some embodiments of the present disclosure, a system for correcting image data of a plurality of distinct images and generating a plurality of stereoscopic three-dimensional (3D) images comprises: a plurality of distinct imaging devices configured to capture the plurality of distinct images, each distinct imaging device of the plurality of distinct imaging devices comprising a distinct optical chain, each distinct optical chain comprising a distinct set of optical properties, and at least one pair of distinct imaging devices disposed in a stereo relation; and a processor configured by a set of executable instructions, storable in relation to a non-transient memory device, to: receive the image data of the plurality of distinct images captured by the plurality of distinct imaging devices; and correct the image data of the plurality of distinct images by dynamically adjusting at least one optical property of each distinct set of optical properties of each distinct optical chain in relation to at least one optical property of another distinct set of optical properties of another distinct optical chain, whereby the plurality of stereoscopic 3D images are providable.

In accordance with some embodiments of the present disclosure, a method of providing a system for correcting image data of a plurality of distinct images and generating plurality of stereoscopic three-dimensional (3D) images comprises: providing a plurality of distinct imaging devices configured to capture the plurality of distinct images, each distinct imaging device of the plurality of distinct imaging devices comprising a distinct optical chain, each distinct optical chain comprising a distinct set of optical properties, and at least one pair of distinct imaging devices disposed in a stereo relation; and providing a processor configured by a set of executable instructions, storable in relation to a non-transient memory device, to: receive the image data of the plurality of distinct images captured by the plurality of distinct imaging devices; and correct the image data of the plurality of distinct images by dynamically adjusting at least one optical property of each distinct set of optical properties of each distinct optical chain in relation to at least one optical property of another distinct set of optical properties of another distinct optical chain, whereby the plurality of stereoscopic 3D images are providable.

In accordance with some embodiments of the present disclosure, a method of correcting image data of a plurality of distinct images and generating plurality of stereoscopic three-dimensional (3D) images by way of a system comprises: providing the system, providing the system comprising: providing a plurality of distinct imaging devices configured to capture the plurality of distinct images, each distinct imaging device of the plurality of distinct imaging devices comprising a distinct optical chain, each distinct optical chain comprising a distinct set of optical properties, and at least one pair of distinct imaging devices disposed in a stereo relation; and providing a processor configured by a set of executable instructions, storable in relation to a non-transient memory device, to: receive the image data of the plurality of distinct images captured by the plurality of distinct imaging devices; and correct the image data of the plurality of distinct images by dynamically adjusting at least one optical property of each distinct set of optical properties of each distinct optical chain in relation to at least one optical property of another distinct set of optical properties of another distinct optical chain, whereby the plurality of stereoscopic 3D images are providable; and activating the system, thereby generating and correcting at least one stereoscopic 3D image.

Some of the features in the present disclosure are broadly outlined in order that the section entitled Detailed Description is better understood and that the present contribution to the art by the present disclosure is better appreciated. Additional features of the present disclosure are described hereinafter. In this respect, understood is that the subject matter of the present disclosure is not limited in its implementation to the details of the components or steps set forth herein or as illustrated in the several figures of the Drawing, but the subject matter is capable of being carried out in various ways which are also encompassed by the present disclosure. Also, understood is that the phraseology and terminology employed herein are for illustrative purposes in the description and are not regarded as limiting.

BRIEF DESCRIPTION OF DRAWING

The above, and other, aspects, features, and advantages of several embodiments of the present disclosure are described in the following Detailed Description as presented in conjunction with the following several figures of the Drawing.

FIG. 7A is a diagram illustrating a rear perspective view of optical paths in relation to the cameras of the augmented optical imaging system, as shown in FIGS. 5A-5E;

FIG. 7B is a diagram illustrating a bottom perspective view of optical paths in relation to the cameras of the augmented optical imaging system, as shown in FIGS. 5A-5E;

FIG. 7C is a diagram illustrating a rear perspective view of optical paths in relation to the module for augmenting an optical imaging system, as shown in FIGS. 6A and 6B;

FIG. 7D is a diagram illustrating a bottom perspective view of optical paths in relation to the module for augmenting an optical imaging system, as shown in FIGS. 6A and 6B;

Figure 1:
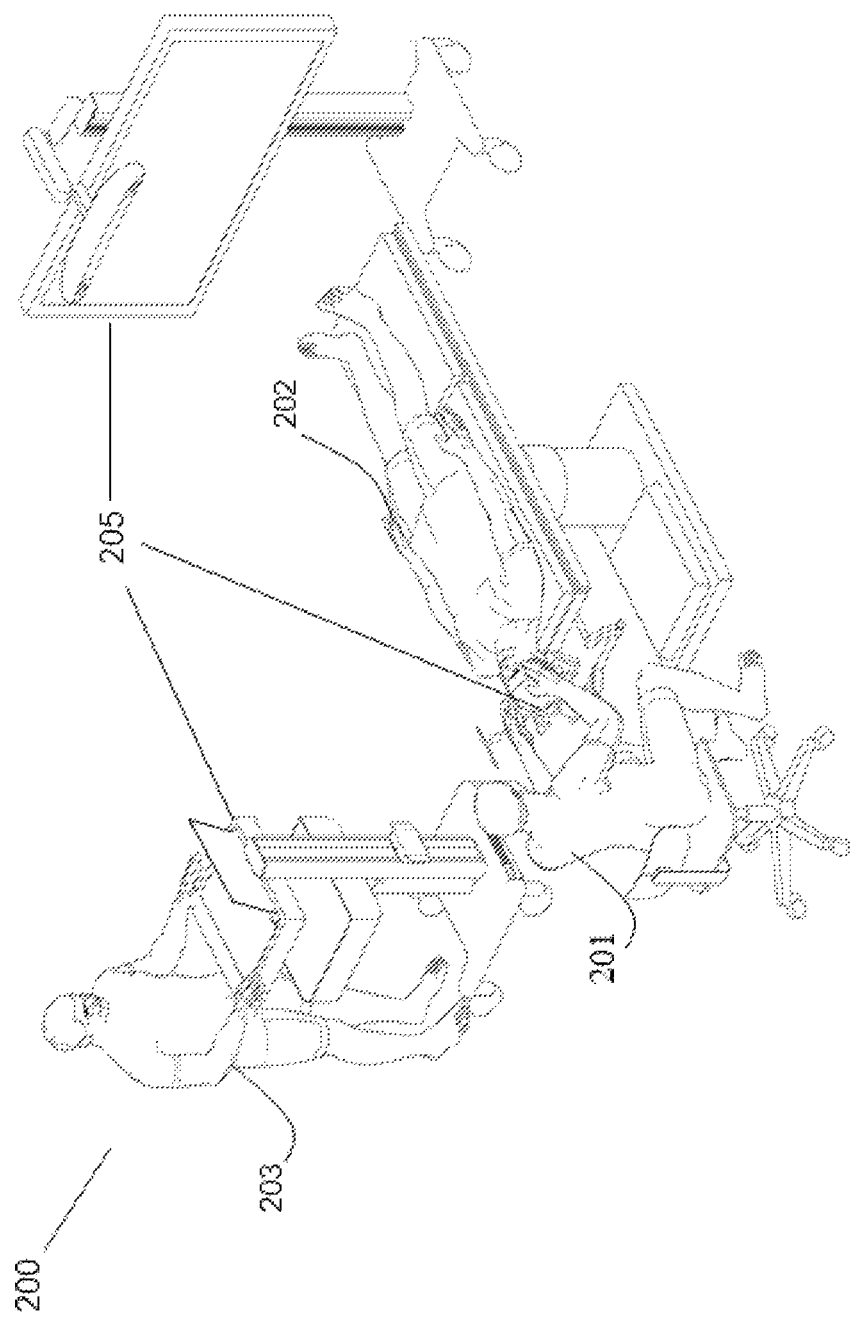
FIG. 1 is a diagram illustrating an example navigation system to support image-guided surgery.

Corresponding reference numerals or characters indicate corresponding components throughout the several figures of the Drawing. Elements in the several figures are illustrated for simplicity and clarity and have not necessarily been drawn to scale. For example, the dimensions of some elements in the figures are emphasized relative to other elements for facilitating understanding of the various presently disclosed embodiments. Also, common but well-understood elements that are useful or necessary in commercially feasible embodiment are often not depicted in order to facilitate a less obstructed view of these various embodiments of the present disclosure. Like reference numerals are used in the several figures of the Drawing to denote like elements and features.

DETAILED DESCRIPTION

In one aspect, the present disclosure involves an optical imaging system for imaging a target during a medical procedure. The optical imaging system comprises: a first camera for capturing a first image of the target; a second wide-field camera for capturing a second image of the target; at least one optional path folding mirror disposed in an optical path between the target and a lens of the second camera; and a processing unit for receiving the first image and the second image, the processing unit being configured to:

apply an image transform to one of the first image and the second image; and combine the transformed image with the other one of the images to produce a stereoscopic image of the target.

In some implementations, the first camera, the second camera, and the at least one optional path folding mirror may be housed within a single housing. In some implementations, the second camera and the at least one optional path folding mirror are included in an add-on module for mounting to the first camera. In some implementations, the at least one optional path folding mirror comprises a first mirror and a second mirror that are selectively positioned based on a position of the lens of the second camera, the first mirror and the second mirror being angled with respect to each other. In some implementations, the first mirror is selectively positioned and angled with respect to the target so as to reflect an image of the target to the second mirror; and the second mirror is selectively positioned and angled so as to reflect the image of the target from the first mirror to the lens of the second camera.

In some implementations, the first camera and the second camera may be positioned such that an optical axis of the first camera is co-planar with the optical axis of the second camera. In some implementations, the image transform comprises a homographic transform. In some implementations, the processing unit is further configured to: determine a working distance between the target and an aperture of the optical imaging system; and determine the image transform based on the working distance. In some implementations, the optical imaging system is configured to be mountable onto a moveable support structure. In some implementations, the optical imaging system further comprises a support connector to enable the optical imaging system to be removably mounted onto the moveable support structure. In some implementations, the moveable support structure comprises one of a robotic arm, a manually-operated support arm, or a moveable support frame.

In some implementations, the optical imaging system further comprises a manual release button that, when actuated, enables the optical imaging system to be positioned manually. In some implementations, the processing unit is responsive to control input received via a user interface. In some implementations, the optical imaging system further comprises one or more light sources. In some implementations, the second camera comprises at least one of fixed zoom optics or fixed focus optics. In some implementations, the second camera is fixedly coupled with the first camera.

In another aspect, the present disclosure involves a method of generating a stereoscopic image of a target in a medical procedure using an optical imaging system. The method comprises: receiving, from a first camera of the optical imaging system, a first image of the target; receiving, from a second camera of the optical imaging system, a second image of the target; applying an image transform to one of the first image and the second image; and combining the transformed image with the other one of the images to produce the stereoscopic image of the target. In some implementations, the method further comprises determining a working distance between the target and an aperture of the optical imaging system; and determining the image transform based on the working distance.

In some implementations, the method further comprises selecting the first homographic transform from a plurality of homographic transforms, wherein selecting comprises, for each of the plurality of homographic transforms: applying the homographic transform to the second image; computing an image correspondence metric between the transformed second image and the first camera, and selecting the homographic transform having a highest value of image correspondence metric from the plurality of homographic transforms as the first homographic transform.

In the present disclosure, the phrase "access port" is intended to refer to a cannula, a conduit, sheath, port, tube, or other structure that is insertable into a subject, in order to provide access to internal tissue, organs, or other biological substances. In some embodiments, an access port directly exposes internal tissue, for example, via an opening or aperture at a distal end thereof, and/or via an opening or aperture at an intermediate location along a length thereof. In other embodiments, an access port provides indirect access, via one or more surfaces that are transparent, or partially transparent, to one or more forms of energy or radiation, such as, but not limited to, electromagnetic waves and acoustic waves.

In the present disclosure, the term "intraoperative" is intended to refer to an action, process, method, event, or step that occurs, or is carried out, during at least a portion of a medical procedure. Intraoperative, as defined herein, is not limited to surgical procedures, and may refer to other types of medical procedures, such as diagnostic and therapeutic procedures.

In the present disclosure, the term "and/or" is intended to cover all possible combinations and sub-combinations of the listed elements, including any one of the listed elements alone, any sub-combination, or all of the elements, and without necessarily excluding additional elements.

In the present disclosure, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

Various medical procedures, such as surgery and diagnostic imaging, employ digital microscopes, which provide magnified views of anatomical structures in real-time. Typically, digital microscope systems incorporate a single main camera (or video-scope) for capturing images which are output to a display for viewing by a surgeon or operator. The main camera provides a single feed of video data, and the frames of the video feed are presented as two-dimensional images. As a result, 3D visualization and, more specifically, depth perception may be absent in these limited digital microscope systems.

In order to generate 3D visualization, a second camera may be added to a digital microscope. The images from the two cameras can be combined to produce stereoscopic views of a surgical site. One of the challenges in providing a 3D capable digital microscope is integrating two cameras such that the microscope maintains a minimal profile in the operative field. A simplistic arrangement of the two cameras side-by-side may render the microscope bulky and may result in significant obstruction of the surgeon's view. A small footprint for the camera modules of the digital microscope offers a large working area for the surgeon.

Furthermore, the size of the cameras and optics may prevent the two cameras of the digital microscope from being arranged close to each other. In particular, physical restrictions to controlling the spacing between the optical paths of the two cameras may exist, thereby resulting in undesirable disparity of images from the cameras, and, as a consequence, thereby resulting in less successful or comfortable 3D visualization experience.

The present disclosure provides an augmented optical imaging system for use in medical applications. The disclosed optical imaging system, for example, is implemented as part of a digital microscope. The system employs a pair of cameras, including a primary camera and an outrigger camera, for imaging a target during a medical procedure. The system further comprises at least one optional path folding mirror which is selectively positioned between the target and a lens of the outrigger camera. The at least one optional path folding mirrors allow the optical path of the outrigger camera to be manipulated, such that the separate optical paths of the two cameras are substantially parallel to each other near the target. The system provides a 3D visualization of the target by combining video/image frames from the two cameras to produce stereoscopic images of the target.

The present disclosure also involves an optics module for extending the functionalities of a digital microscope system. The disclosed optics module may comprise an add-on component to an existing optical imaging device, such as a digital microscope. The module comprises an outrigger camera and at least one optional path folding mirror. The at least one optional path folding mirror is disposed in an optical path between a lens of the outrigger camera and a target being imaged. The module is configured to couple with the optical imaging device. For example, the module defines a chamber for receiving a primary camera, e.g., a video-scope, of the optical imaging device, such that both the primary camera and the outrigger camera are directed towards the target when the module is secured to the optical imaging device. With a minimal profile in the working field, the disclosed optics module allows the combined optical imaging system to produce 3D visualization of a target.

Referring to FIG. 1, this diagram illustrates an example navigation system 200, in accordance with an embodiment of the present disclosure. The example navigation system 200 is used to support image-guided surgery. A surgeon 201 conducts a surgery on a patient 202 in an operating room environment. A medical navigation system 205 comprises an equipment tower, tracking system, displays, and tracked instruments to assist the surgeon 201 during a procedure. An operator 203 may also be present to operate, control, and assist the medical navigation system 205.

Figure 2:
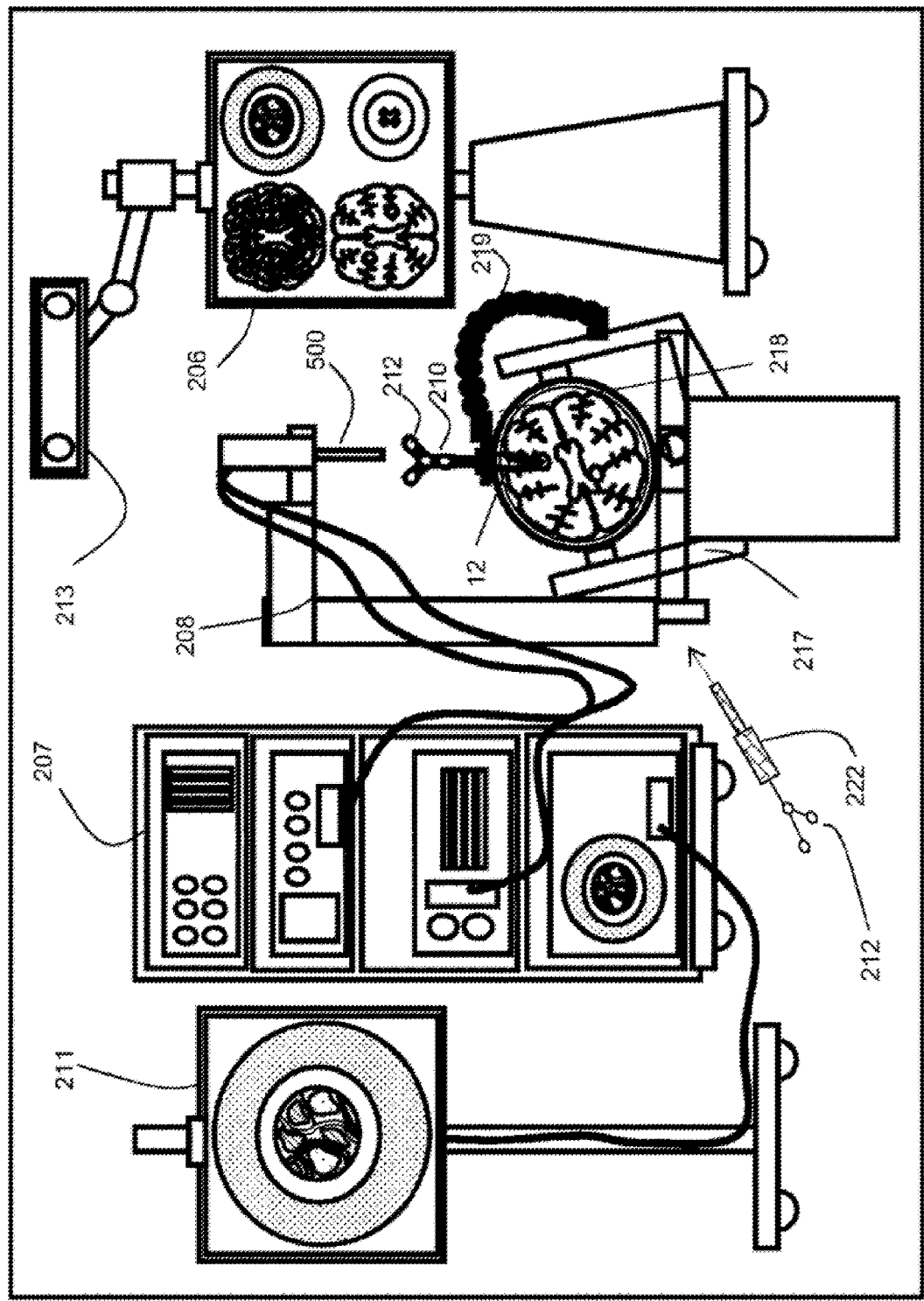
FIG. 2 is a diagram illustrating components of an example navigation system.

Referring to FIG. 2, this diagram illustrates components of an example medical navigation system 205, in accordance with an embodiment of the present disclosure. The augmented optical imaging system is used in the context of the medical navigation system 205. The medical navigation system 205 comprises one or more displays 206, 211 for displaying video images, an equipment tower 207, and a positioning system 208, such as a medical arm, which may support an optical imaging system 500. One or more of the displays 206, 211 comprises a touch-sensitive display for receiving touch input. The equipment tower 207 is coupled with, e.g., mounted, on a frame, such as a rack or cart, and contains a power supply and a computer/controller that execute planning software, navigation software, and/or other software to manage the positioning system 208. In some examples, the equipment tower 207 comprises a single tower configuration operating with dual displays 206, 211; however, other configurations, e.g., a dual tower, a single display etc., are also encompassed by the present disclosure.

Still referring to FIG. 2, a portion of the patient's anatomy may be held in place by a holder. For example, the patient's head and brain may be held in place by a head holder 217. An access port 12 and associated introducer 210 may be inserted into the head, to provide access to a surgical site in the head. The optical imaging system 500 may be used to view down the access port 12 at a sufficient magnification to allow for enhanced visibility down the access port 12. The output of the optical imaging system 500 may be received by one or more computers or controllers to generate a view that may be depicted on a visual display, e.g., one or more displays 206, 211.

Still referring to FIG. 2, in some examples, the navigation system 205 comprises a tracked pointer 222. The tracked pointer 222, which may include markers 212 to enable tracking by a tracking camera 213, is used to identify points, e.g., fiducial points, on a patient. An operator, typically a nurse or the surgeon 201, uses the tracked pointer 222 to identify the location of points on the patient 202, in order to register the location of selected points on the patient 202 in the navigation system 205. In some embodiments, a guided robotic system with closed loop control is used as a proxy for human interaction. Guidance to the robotic system is provided by any combination of input sources, such as image analysis, tracking of objects in the operating room using markers placed on various objects of interest, and/or any other suitable robotic system guidance techniques.

Still referring to FIG. 2, fiducial markers 212 are coupled with the introducer 210 for tracking by the tracking camera 213, thereby providing positional information of the introducer 210 from the navigation system 205. In some examples, the fiducial markers 212 are, alternatively, or additionally, coupled with the access port 12. In some examples, the tracking camera 213 comprises a 3D infrared optical tracking stereo camera. In some other examples, the tracking camera 213 comprises an electromagnetic system (not shown), such as a field transmitter using one or more receiver coils located on the tool(s) to be tracked. A known profile of the electromagnetic field and known position of receiver coil(s) relative to each other may be used to infer the location of the tracked tool(s) using the induced signals and their phases in each of the receiver coils.

Still referring to FIG. 2, location data of the positioning system 208 and/or the access port 12 is determined by the tracking camera 213 by detection of the fiducial markers 212 coupled with, such as placed on, or otherwise in fixed to, e.g., in rigid connection, any of the positioning system 208, the access port 12, the introducer 210, the tracked pointer 222, and/or other tracked instruments. The fiducial marker(s) 212 comprise active or passive markers. Displays 206, 211 provide an output of the computed data of the navigation system 205. In some examples, the output provided by the displays 206, 211 comprise axial, sagittal, and coronal views of patient anatomy as part of a multi-view output.

Still referring to FIG. 2, the active or passive fiducial markers 212 are coupled with, e.g., placed on, tools, such as the access port 12 and/or the optical imaging system 500, to be tracked, to determine the location and orientation of these tools using the tracking camera 213 and navigation system 205. The markers 212 are captured by a stereo camera of the tracking system to give identifiable points for tracking the tools. A tracked tool is defined by a grouping of markers 212, thereby defining a rigid body to the tracking system. Defining the rigid body to the tracking system, in turn, is used to determine the position and/or orientation in 3D of a tracked tool in a virtual space. The position and orientation of the tracked tool in 3D is tracked in six degrees of freedom, e.g., x, y, z coordinates and pitch, yaw, roll rotations, in five degrees of freedom, e.g., x, y, z, coordinate and two degrees of free rotation, but preferably tracked in at least three degrees of freedom, e.g., tracking the position of the tip of a tool in at least x, y, z coordinates. In typical use with navigation systems, at least three markers 212 are provided on a tracked tool to define the tool in virtual space; however, four or more markers 212 can be used.

Still referring to FIG. 2, camera images, capturing the markers 212, are logged and tracked, for example, by a closed circuit television (CCTV) camera. The markers 212 are selected to enable or assist in segmentation in the captured images. For example, infrared (IR)-reflecting markers and an IR light source from the direction of the camera are used. In some examples, the spatial position and orientation of the tracked tool and/or the actual and desired position and orientation of the positioning system 208 are determined by optical detection using a camera. The optical detection is performed by using an optical camera, thereby rendering the markers 212 optically visible.

Still referring to FIG. 2, in some examples, the markers 212, e.g., reflectospheres, are used in combination with a suitable tracking system, to determine the spatial positioning position of the tracked tools within the operating theatre. Different tools and/or targets are provided with respect to sets of markers 212 in different configurations. Differentiation of the different tools and/or targets and their corresponding virtual volumes is possible based on the specification configuration and/or orientation of the different sets of markers 212 relative to one another, enabling each such tool and/or target to have a distinct individual identity within the navigation system 205. The individual identifiers provide information to the system, such as information relating to the size and/or shape of the tool within the system. The identifier also provides additional information, such as the tool's central point or the tool's central axis, among other information. The virtual tool is also determinable from a database of tools stored in, or provided to, the navigation system 205. The markers 212 are tracked relative to a reference point or reference object in the operating room, such as the patient 202.

Still referring to FIG. 2, in some examples, the markers 212 comprise printed or 3D configurations that used for detection by an auxiliary camera, such as a wide-field camera (not shown) and/or the optical imaging system 500. Printed markers may also be used as a calibration pattern, for example to provide distance information, e.g., 3D distance information, to an optical detector. Printed identification markers have configurations, such as concentric circles with different ring spacing and/or different types of bar codes, among other configurations. In some examples, in addition to or in place of using markers 212, the contours of known objects, e.g., the side of the access port 12, could be captured by and identified using optical imaging devices and the tracking system.

Still referring to FIG. 2, a guide clamp 218 (or more generally a guide) for holding the access port 12 is provided. The guide clamp 218 allows the access port 12 to be held at a fixed position and orientation while freeing up the surgeon's hands. An articulated arm 219 is provided to hold the guide clamp 218. The articulated arm 219 has up to six degrees of freedom to position the guide clamp 218. The articulated arm 219 is lockable to fix its position and orientation, e.g., once a desired position is achieved. The articulated arm 219 is coupled with, e.g., attached, or attachable to, a point based on the patient head holder 217, or another suitable point, e.g., on another patient support, such as on the surgical bed, to ensure that, when locked in place, the guide clamp 218 does not move relative to the patient's head.

Still referring to FIG. 2, in a surgical operating room/theatre, setup of a navigation system is relatively complicated; and many pieces of equipment associated with the surgical procedure as well as elements of the navigation system 205 exist. Further, setup time typically increases as more equipment is added. To assist in addressing this, the navigation system 205 comprises two additional wide-field cameras to enable video overlay information. Video overlay information is then be inserted into displayed images, such as images displayed on one or more of the displays 206, 211. The overlay information illustrates the physical space where accuracy of the 3D tracking system (which is typically part of the navigation system) is greater, illustrates the available range of motion of the positioning system 208 and/or the optical imaging system 500, and/or assists in guiding head positioning and/or patient positioning.

Still referring to FIG. 2, the navigation system 205 provides tools to the neurosurgeon that assist in providing more relevant information to the surgeon and assist in improving performance and accuracy of port-based neurosurgical operations. Although described in the present disclosure in the context of port-based neurosurgery, e.g., for removal of brain tumors and/or for treatment of intracranial hemorrhages (ICH), the navigation system 205 is also suitable for one or more of the following procedures: brain biopsy, functional/deep-brain stimulation, catheter/shunt placement (in the brain or elsewhere), open craniotomies, and/or endonasal/skull-based/ear-nose-throat (ENT) procedures, among others. The same navigation system 205 is used for carrying out any, or all, of these procedures, with, or without, modification, as appropriate.

Still referring to FIG. 2, in some examples, the tracking camera 213 may be part of any suitable tracking system. In some examples, the tracking camera 213 (and any associated tracking system that uses the tracking camera 213) may be replaced with any suitable tracking system which may or may not use camera-based tracking techniques. For example, a tracking system that does not use the tracking camera 213, such as a radiofrequency tracking system, may be used with the navigation system 205.

Figure 3:
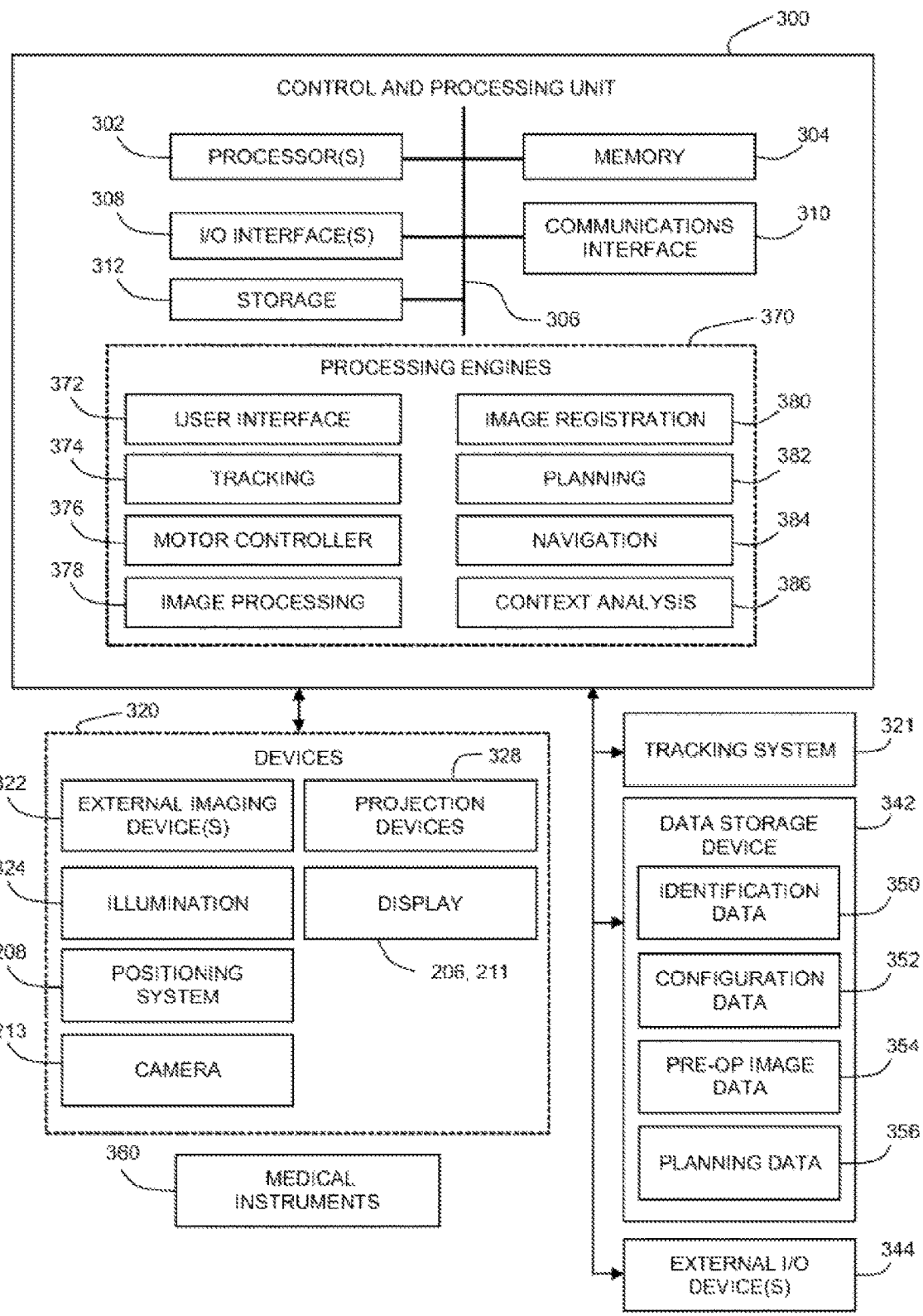
FIG. 3 is a block diagram illustrating an example control and processing system usable in the example navigation system, as shown in FIGS. 1 and 2.

Referring to FIG. 3, this block diagram illustrates a control and processing system 300 that usable in the medical navigation system 205, as shown in FIG. 2, e.g., as part of the equipment tower 207, in accordance with an embodiment of the present disclosure. The control and processing system 300 comprises one or more processors 302, a memory 304, a system bus 306, one or more input/output interfaces 308, a communications interface 310, and storage device 312. The control and processing system 300 interfaces with other external devices, such as a tracking system 321, data storage 342, and external user input and output devices 344, such as one or more of a display, keyboard, mouse, sensors attached to medical equipment, foot pedal, a microphone, and a speaker. Data storage 342 may be any suitable data storage device, such as a local or remote computing device, e.g., a computer, hard drive, digital media device, or server, having a database stored thereon. The data storage device 342 comprises identification data 350 for identifying one or more medical instruments 360 and configuration data 352 that associates customized configuration parameters with one or more medical instruments 360. The data storage device 342 stores preoperative image data 354 and/or medical procedure planning data 356. Although the data storage device 342 is shown as a single device, understood is that, in other embodiments, the data storage device 342 comprises multiple storage devices.

Still referring to FIG. 3, the medical instruments 360 are identifiable by the control and processing unit 300. The medical instruments 360 are coupled with, and controlled by, the control and processing unit 300. Alternatively, the medical instruments 360 are operated, or otherwise employed, independent of the control and processing unit 300. The tracking system 321 is employed to track one or more medical instruments 360 and spatially register the one or more tracked medical instruments to an intraoperative reference frame. For example, the medical instruments 360 comprise tracking markers, such as tracking sphere, that are recognizable by the tracking camera 213. In one example, the tracking camera 213 comprises an infrared (IR) tracking camera. In another example, a sheath placed over a medical instrument 360 is coupled with, and controlled by, the control and processing unit 300. The control and processing unit 300 also interfaces with a number of configurable devices and intraoperatively reconfigures one or more of such devices based on configuration parameters obtained from configuration data 352. Examples of the devices 320 include, but are not limited to, one or more external imaging devices 322, one or more illumination devices 324, the positioning system 208, the tracking camera 213, one or more projection devices 328, and one or more displays 206, 211.

Still referring to FIG. 3, exemplary aspects of the disclosure are implemented via the processor(s) 302 and/or the memory 304. For example, the functionalities described herein are partially implemented via hardware logic in the processor 302 and partially use the instructions, as one or more processing modules or engines 370, stored in the memory 304. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately, in some examples, the processing modules 370 are stored in the memory 304; and the processing modules 370 are collectively referred as the processing modules 370. In some examples, a plurality of modules 370 are used together to perform a function. Although depicted as separate modules 370, the modules 370 may be embodied as a unified set of computer-readable instructions, e.g., stored in the memory 304, rather than distinct sets of instructions.

Figure 4A:
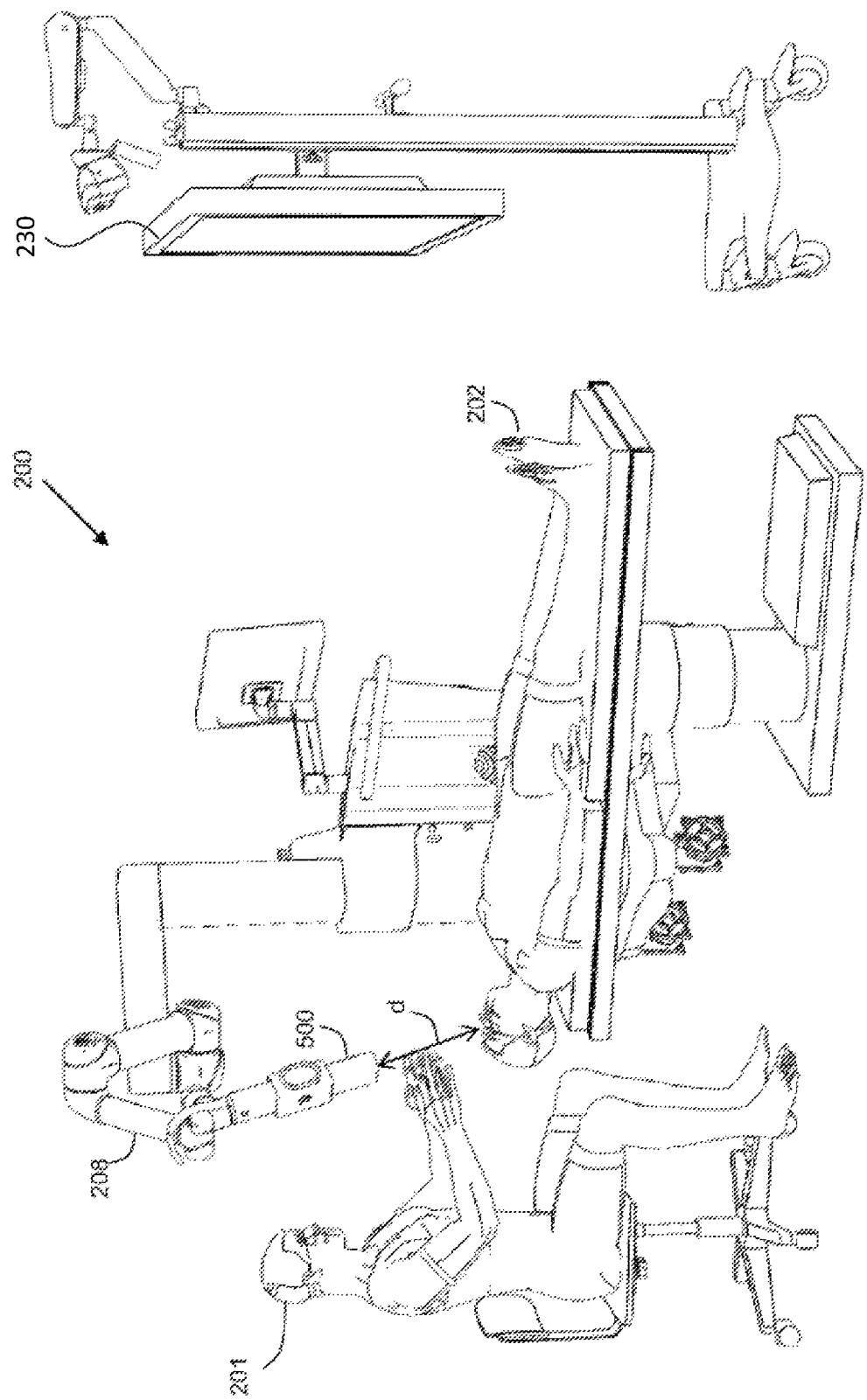
FIG. 4A is a diagram illustrating use of an example optical imaging system during a medical procedure.

Referring to FIG. 4A, this diagram illustrates use of an example optical imaging system 500 in a medical procedure, in accordance with an embodiment of the present disclosure. Although the optical imaging system 500 is shown as being used in the context of a navigation system environment 200, e.g., using a navigation system as described above, the optical imaging system 500 may also be used outside of a navigation system environment. An operator, typically a surgeon 201, uses the imaging system 500 to observe the surgical site, e.g., to look down an access port. The optical imaging system 500 is coupled with a positioning system 208, such as a controllable and adjustable robotic arm. The position and orientation of the positioning system 208, imaging system 500, and/or access port are tracked using a tracking system, such as described for the navigation system 205.

Still referring to FIG. 4A, a distance between the optical imaging system 500 (more specifically, the aperture of the optical imaging system 500) and the viewing target is referred as the working distance. The optical imaging system 500 is configured for use in a predefined range of working distance, e.g., in the range of between approximately 15 centimeters and approximately 75 centimeters. If the optical imaging system 500 is mounted on the positioning system 208, the actual available range of working distance may be dependent on both the working distance of the optical imaging system 500 as well as the workspace and kinematics of the positioning system 208. In some embodiments, the optical imaging system 500 comprises a manual release button that, when actuated, enables the optical imaging system to be positioned manually. For example, the controller of the optical imaging system 500 may be responsive to manual control input received via a user interface.

Figure 4B:
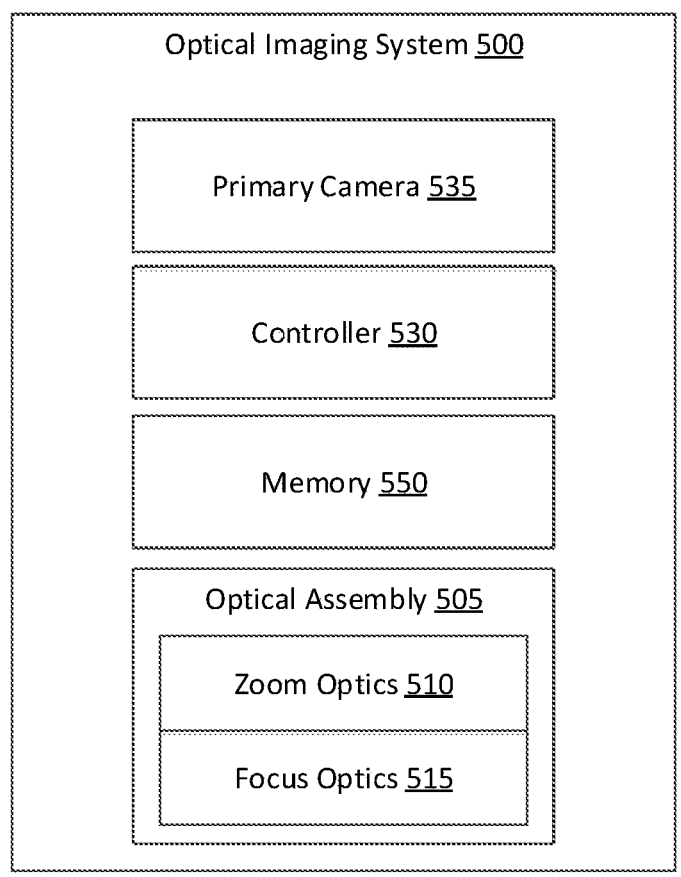
FIG. 4B is a block diagram illustrating components of an example optical imaging system.
Figure 5C:
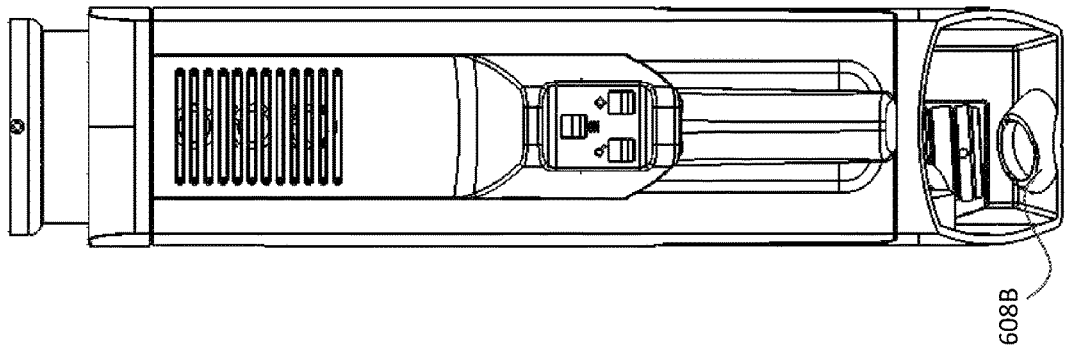
FIG. 5C is a diagram illustrating a rear view of an example augmented optical imaging system, as shown in FIGS. 5A and 5B.
Figure 5B:
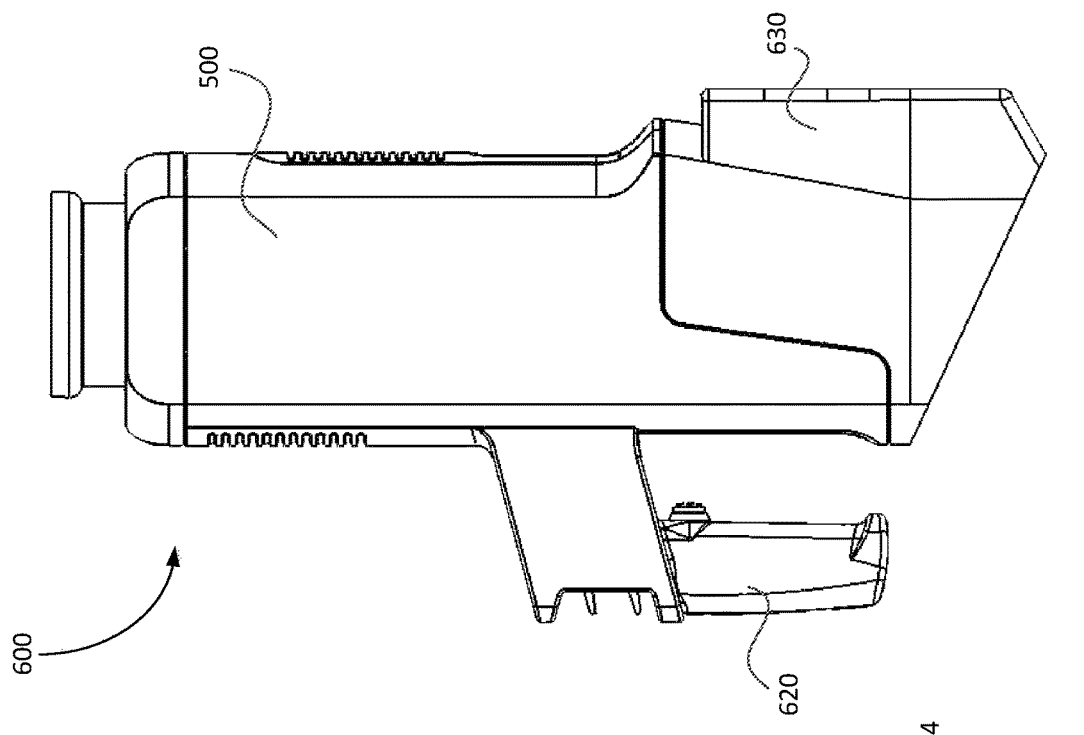
FIG. 5B is a diagram illustrating a side view of an example augmented optical imaging system, as shown in FIG. 5A.
Figure 5A:
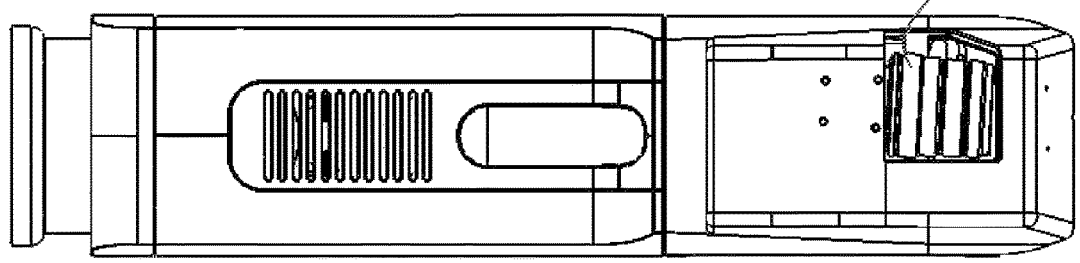
FIG. 5A is a diagram illustrating a front view of an example augmented optical imaging system.
Figure 5D:
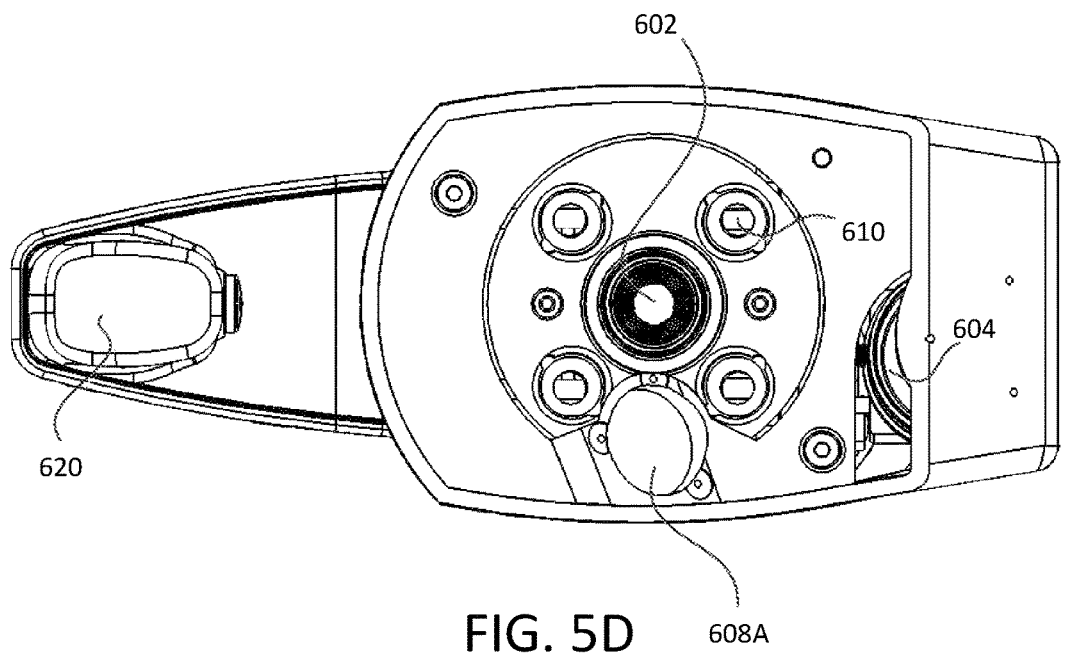
FIG. 5D is a diagram illustrating a bottom view of an example augmented optical imaging system, as shown in FIGS. 5A-5C.
Figure 5E:
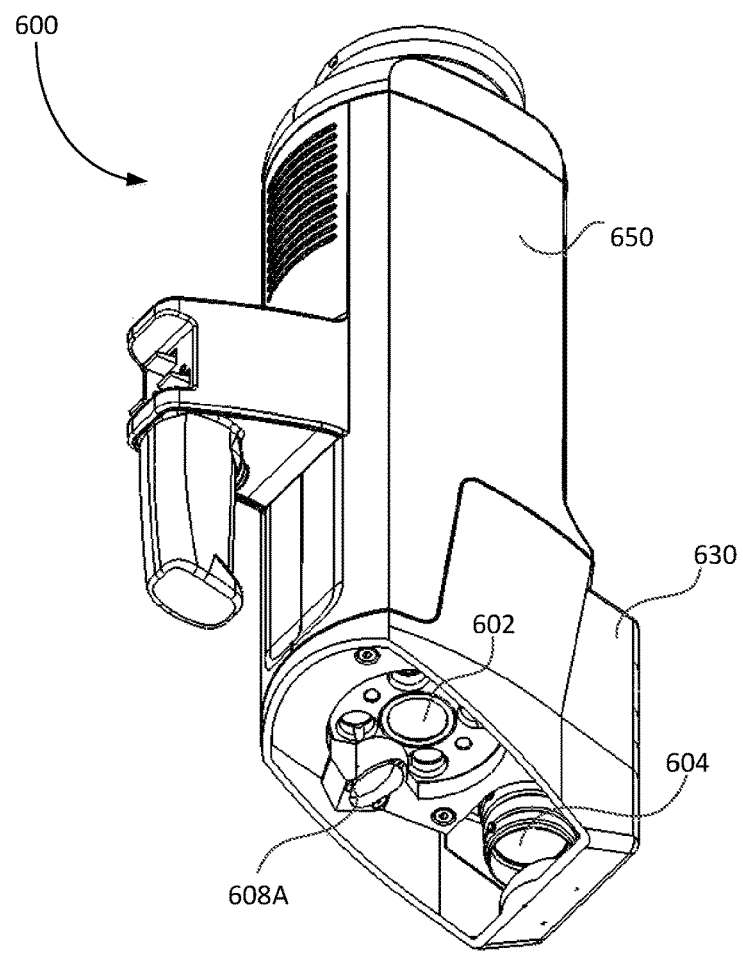
FIG. 5E is a diagram illustrating a perspective view of an example augmented optical imaging system, as shown in FIGS. 5A-5D.

Referring to FIG. 4B, this diagram illustrates components of an example optical imaging system 500, in accordance with an embodiment of the present disclosure. The optical imaging system 500 comprises a primary camera (or videoscope) 535. The primary camera 535 comprises a high-definition (HD) camera that captures image data from the optical assembly. The optical imaging system 500 further comprises an optical assembly 505. The optical assembly 505 comprises optics, e.g., lenses, optical fibers, etc., for focusing and zooming on the viewing target. The optical assembly 505 comprises zoom optics 510 and focus optics 515. Each of the zoom optics 510 and focus optics 515 are independently moveable within the optical assembly, in order to adjust the zoom and focus, respectively. The optical assembly 505 comprises an aperture which may be adjustable.

Still referring to FIG. 4B, the optical imaging system 500 also comprises a memory 550 and a controller 530 coupled with the memory 550. The controller 530 comprises one or more processors, e.g. micro-processors, programmable logic devices, e.g., field-programmable gate arrays, or FPGAs, application-specific integrated circuits (ASICs), or combinations thereof. In at least some embodiments, the controller 530 is configured to control operation of a zoom actuator and a focus actuator. The controller 530 receives control input indicating a desired zoom and/or focus and, in response to receiving the input, the controller 530 causes the zoom actuator and/or the focus actuator to respectively move the zoom optics 510 and focus optics 515.

Still referring to FIG. 4B, the controller 530 is also configured to control operation of the primary camera 535. The primary camera 535 outputs camera data to the controller 530, which in turn transmits the data to an external system for viewing. The captured images are viewed on larger displays and are displayed together with other relevant information, such as a wide-field view of the surgical site, navigation markers, etc.

Still referring to FIG. 4B, in at least some embodiments, the primary camera 535, the optical assembly 505 (including the zoom optics 510 and focus optics 515), the controller 530, and the memory 550 are housed within a single housing of the optical imaging system 500. The housing is provided with a frame on which trackable markers are mounted to enable tracking by a navigation system. The optical imaging system 500 is mountable on a moveable support structure, such as a positioning system, e.g., robotic arm of a navigation system, a manually operated support arm, a ceiling-mounted support, a moveable frame, or other support structure. In some embodiments, the optical imaging system 500 comprises a support connector, such as a mechanical coupling, to enable removably coupling the optical imaging system 500 with the support structure.

Referring to FIGS. 5A-5E, together, these diagrams illustrate different views of an example augmented optical imaging system 600, in accordance with some embodiments of the present disclosure. The augmented optical imaging system 600 comprises one or more of the components of the optical imaging system 500. In particular, the augmented optical imaging system 600 comprises a primary camera 602 for capturing an image of a target, zoom and focus optics, one or more light sources 610, and a controller (not shown) for controlling operation of the primary camera 602 and zoom, focus, and/or auxiliary optics.

Still referring to FIGS. 5A-5E, together, in addition to these components, the augmented optical imaging system 600 comprises a 3D optics module 630 which extends the functionalities of the optical imaging system 500. In particular, the 3D optics module 630 comprises an add-on component to the optical imaging system 500. In some embodiments, the 3D optics module 630 is separable from the optical imaging system 500. For example, the 3D optics module 630 comprises a separate device/module configured to couple with the optical imaging system 500 or components thereof, such as the primary camera 602. In such embodiments, the optical imaging system 500 refers to that part of the augmented optical imaging system 600 which is separate from the 3D optics module 630. The 3D optics module 630 enables the augmented optical imaging system 600 to obtain 3D information of a viewing target.

Referring to FIGS. 6A-6B and 7C-7D, together, the 3D optics module 630 comprises a secondary camera 604, e.g., an outrigger camera, for capturing an image of a target and a pair of optional path folding mirrors 608A and 608B, in accordance with some embodiments of the present disclosure. The secondary camera 604 has a wide-field view and at least one of fixed zoom optics, fixed focus optics, and digital zoom capability. Each optional path folding mirror of the optional path folding mirrors 608A and 608B is positioned in a spaced relation to the other optional path folding mirror of the optional path folding mirrors 608A and 608B. Specifically, Each optional path folding mirror of the optional path folding mirrors 608A and 608B is angled in relation to the other optional path folding mirror of the optional path folding mirrors 608A and 608B, wherein the optional path folding mirrors 608A and 608B are disposed in an optical path between a target being imaged by the secondary camera 604 and a lens of the secondary camera 604. That is, light reflected from a surface of the imaged target traverses a path that includes the optional path folding mirrors 608A and 608B. The optical path of the secondary camera 604, thus, includes, at least, a first segment S1 disposed between the target and a reflective surface of a first optional path folding mirror 608A, a second segment S2 disposed between the reflective surface of the first optional path folding mirror 608A and a reflective surface of a second optional path folding mirror 608B, and a third segment S3 between the reflective surface of the second optional path folding mirror 608B and a lens of the secondary camera 604. Accordingly, in at least some embodiments, the optional path folding mirrors 608A and 608B are selectively positioned based on a position of the lens of the secondary camera 604. This optical path is shown in FIGS. 7C-7D.

Figure 6B:
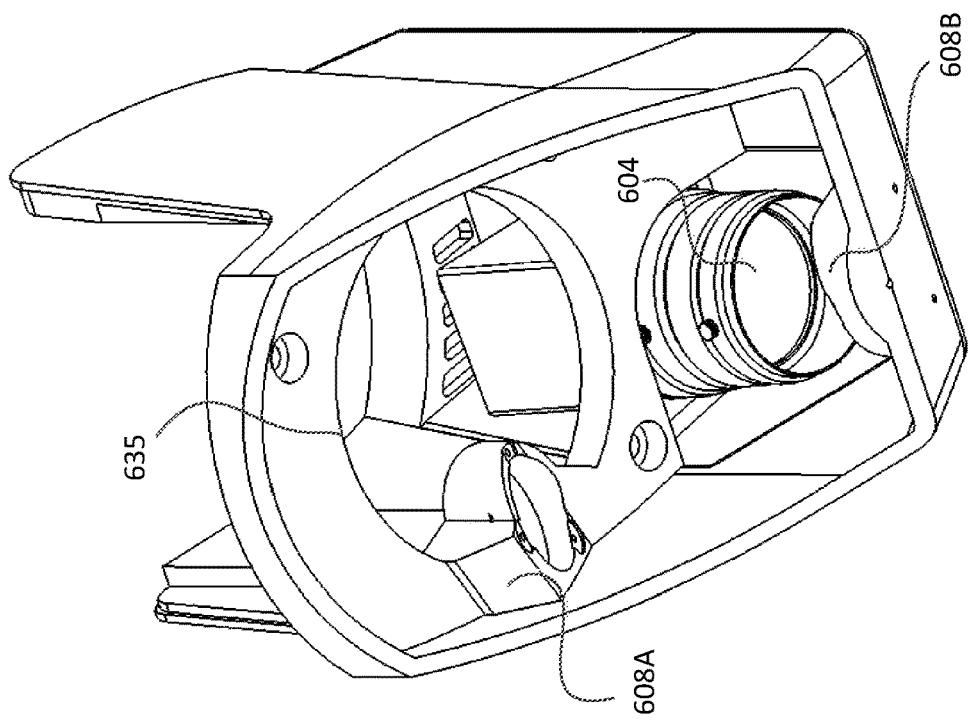
FIG. 6B is a diagram illustrating another perspective view of an example module for augmenting an optical imaging system, as shown in FIG. 6A.
Figure 6A:
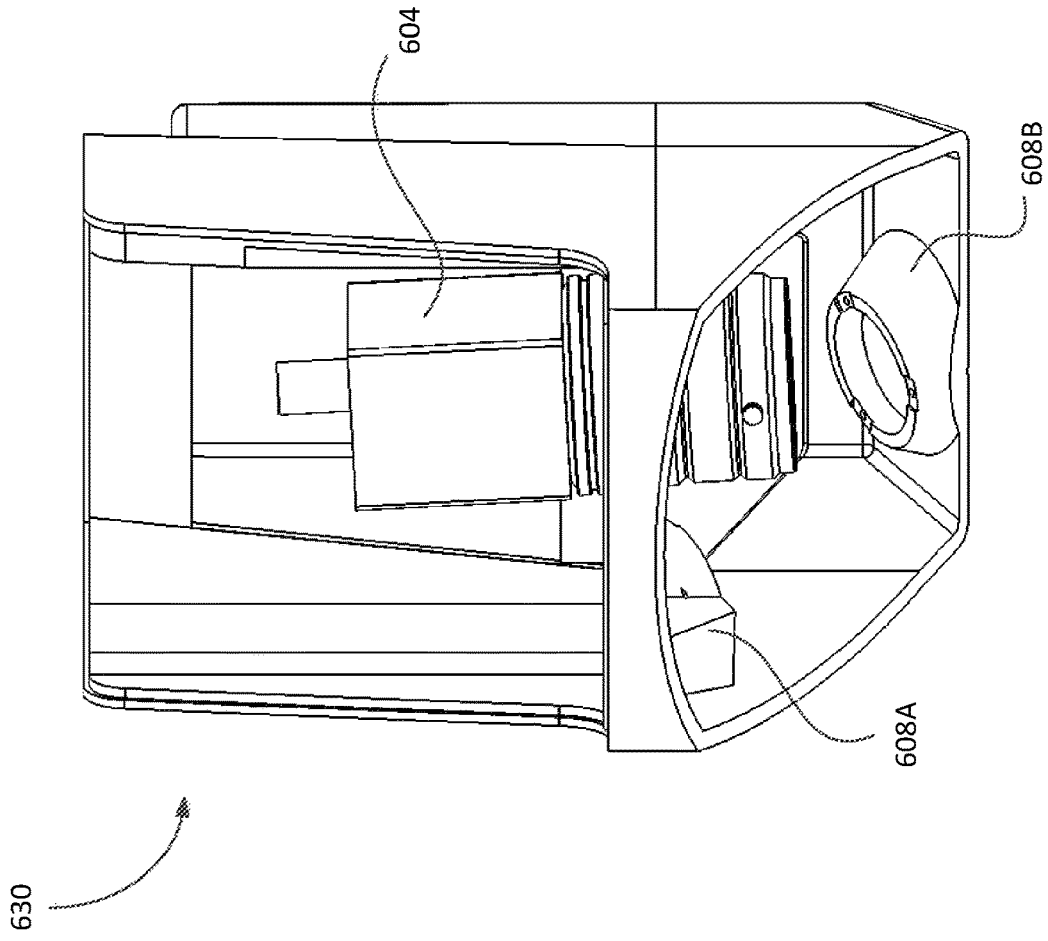
FIG. 6A is a diagram illustrating a perspective view of an example module for augmenting an optical imaging system.

Still referring to FIGS. 6A-6B and 7C-7D, together, the 3D optics module 630 is configured to couple with an optical imaging system in order to augment the functionalities of the optical imaging system. In particular, the 3D optics module 630 is directly affixed to an optical imaging system and secured thereto by a suitable fastening mechanism. As shown in FIG. 6B, the 3D optics module 630 defines a chamber/bore which is sized to receive the primary camera 602 when the 3D optics module 630 is secured to the optical imaging system. The optics of the primary camera 602 align with the opening 635 defined on the 3D optics module 630. In some embodiments, the primary camera 602 extends through the opening 635 when the 3D optics module 630 is secured to the optical imaging system.

Referring back to FIGS. 5A-5E, together, a controller of the augmented optical imaging system 600 is configured to receive a first image from the primary camera 602 and a second image from the secondary camera 604. For example, the primary camera 602 and secondary camera 604 may acquire real-time camera data, e.g., videos, images, etc., depicting a target. In at least some embodiments, the primary camera 602 and the secondary camera 604 are positioned such that the optical axis of the primary camera 602 is co-planar with the optical axis of the secondary camera 604. The primary camera 602 is offset both vertically and horizontally relative to the secondary camera 604. In some embodiments, the primary camera 602 and the secondary camera 604 are offset only horizontally.

Figure 8:
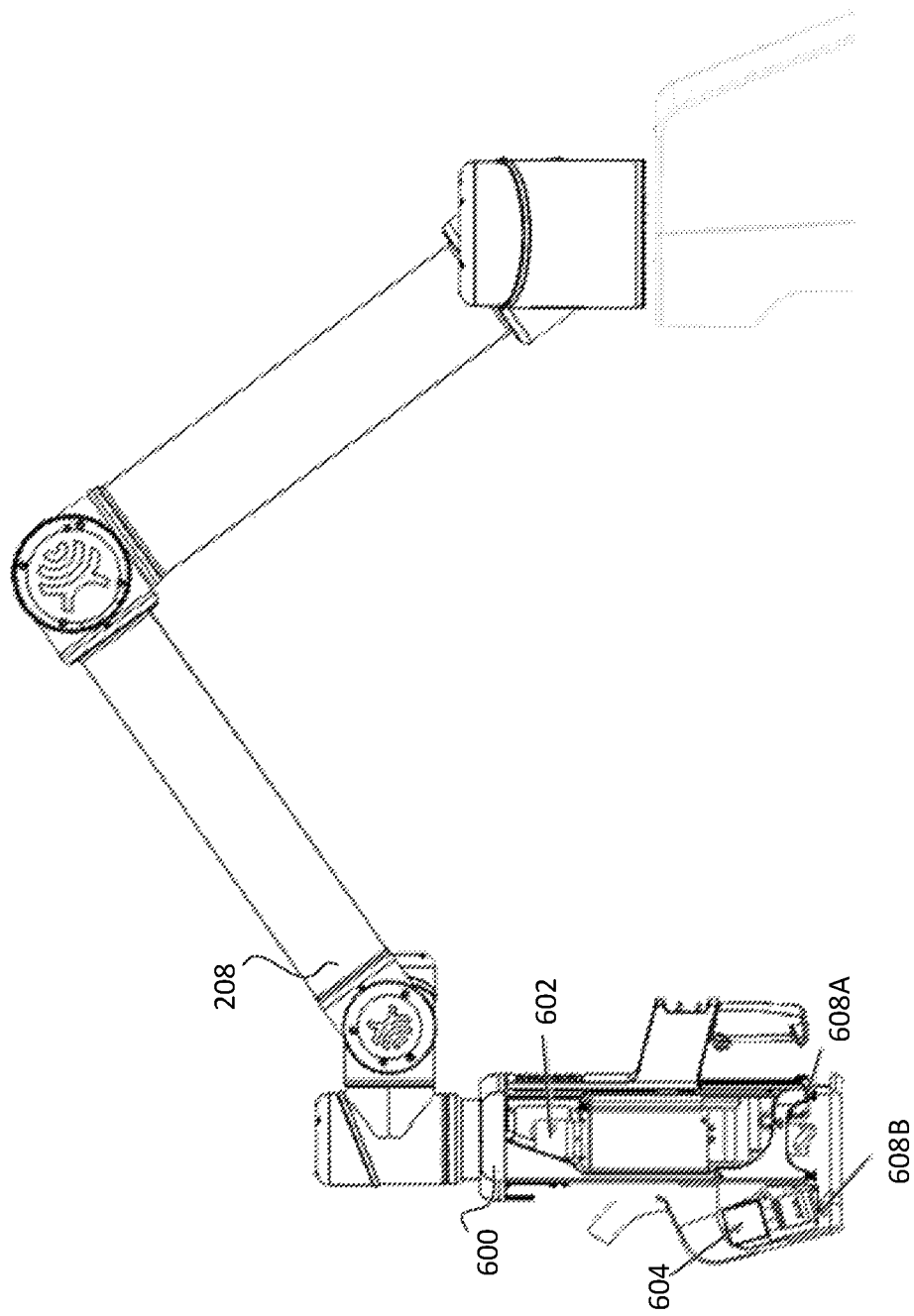
FIG. 8 is a diagram illustrating a partial side cross-sectional view of the augmented optical imaging system coupled with a positioning system.

Referring to FIG. 8, this diagram illustrates the augmented optical imaging system 600 mounted to a positioning system 208, e.g., a robotic arm, of a navigation system, in accordance with an embodiment of the present disclosure. The augmented optical imaging system 600 is shown with a housing enclosing the zoom and focus optics, the primary camera 602, the secondary camera 604, and a pair of optional path folding mirrors 608A and 608B, the secondary camera 604 angled with respect to the primary camera 602. In particular, the primary camera 602 is positioned substantially vertically within the housing of the augmented optical imaging system while the secondary camera 604 is positioned at an angle with respect to the vertical. The optional path folding mirrors 608A and 608B are disposed in the 3D optics module 630 such that the optical path for the secondary camera 604 does not intersect the optical path for the primary camera 602. Specifically, the optional path folding mirrors 608A and 608B are positioned so that the optical path for the secondary camera 604 does not obstruct the substantially vertical line of sight of the primary camera 602.

Figure 9:
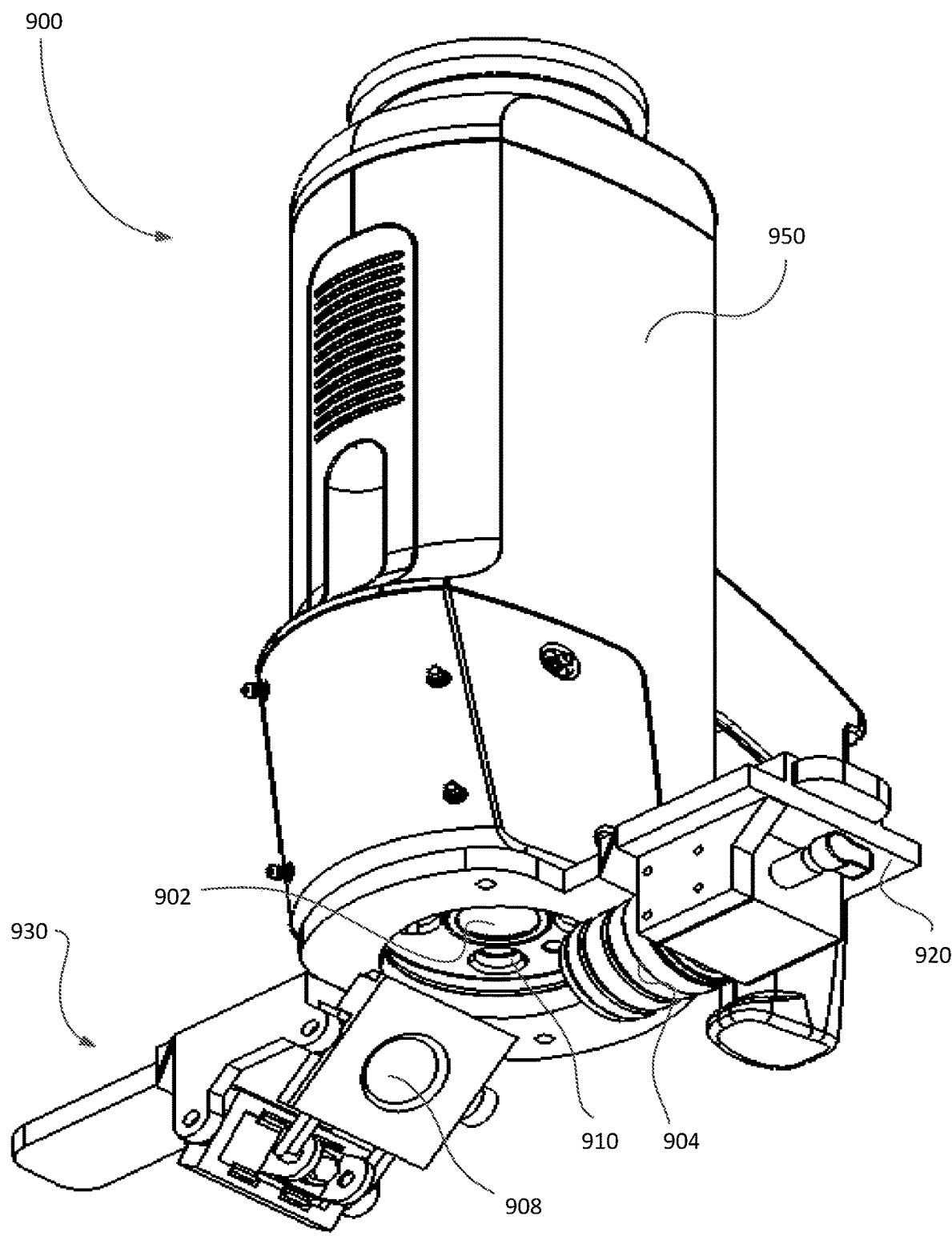
FIG. 9 is a diagram illustrating a perspective view of another example augmented optical imaging system.

Referring to FIG. 9, this diagram illustrates a perspective view of another example augmented optical imaging system 900, in accordance with an embodiment of the present disclosure. The augmented optical imaging system 900 is incorporated into a digital microscope system, and more generally, a medical navigation system. The augmented optical imaging system 900 comprises an optical imaging system 950 and a 3D optics module 930. The optical imaging system 950 comprises at least a primary camera 902 for imaging a target and one or more light sources 910. The 3D optics module 930 is either integral to the optical imaging system 950 or is a separable add-on component which can be secured to the optical imaging system 950. The 3D optics module 930 comprises a secondary camera 904 and a single optional path folding mirror 908. The position of the optional path folding mirror 908 is variable. For example, in some embodiments, a relative angle of the reflective surface of the optional path folding mirror 908 with respect to a lens of the secondary camera 904 is adjustable, either manually or via a control input. An actuator associated with the optional path folding mirror 908 is controlled by a controller (not shown) of the augmented optical imaging system 900. In other embodiments (not shown), the actuator is manually moved to configure the relative angle.

Still referring to FIG. 9, the secondary camera 904 is substantially orthogonally positioned in relation to the primary camera 902. In particular, the primary camera 902 is vertically directed downward, while the secondary camera 904 is substantially horizontally directed. The 3D optics module 930 comprises a plate 920 which is securable to the optical imaging system 950. The plate 920 is generally planar and elongate, and is disposed generally orthogonal to the optical imaging system 950. That is, the plate 920 is substantially horizontally disposed when secured to the optical imaging system 950. The secondary camera 904 is affixed to the plate 920.

Still referring to FIG. 9, the optional path folding mirror 908 is disposed in an optical path between a target being imaged and a lens of the secondary camera 904. That is, an optical path of the secondary camera 904 traverses a path defined by a first segment disposed between the target and a reflective surface of the optional path folding mirror 908 and a second segment disposed between the reflective surface of the optional path folding mirror 908 and a lens of the secondary camera 904. The optional path folding mirror 908 is located on the 3D optics module 930 such that the optional path folding mirror 908 does not obstruct a (vertical) line of sight of the primary camera 902. That is, the optional path folding mirror 908 does not interfere with an optical path of the primary camera 902.

Figure 10:
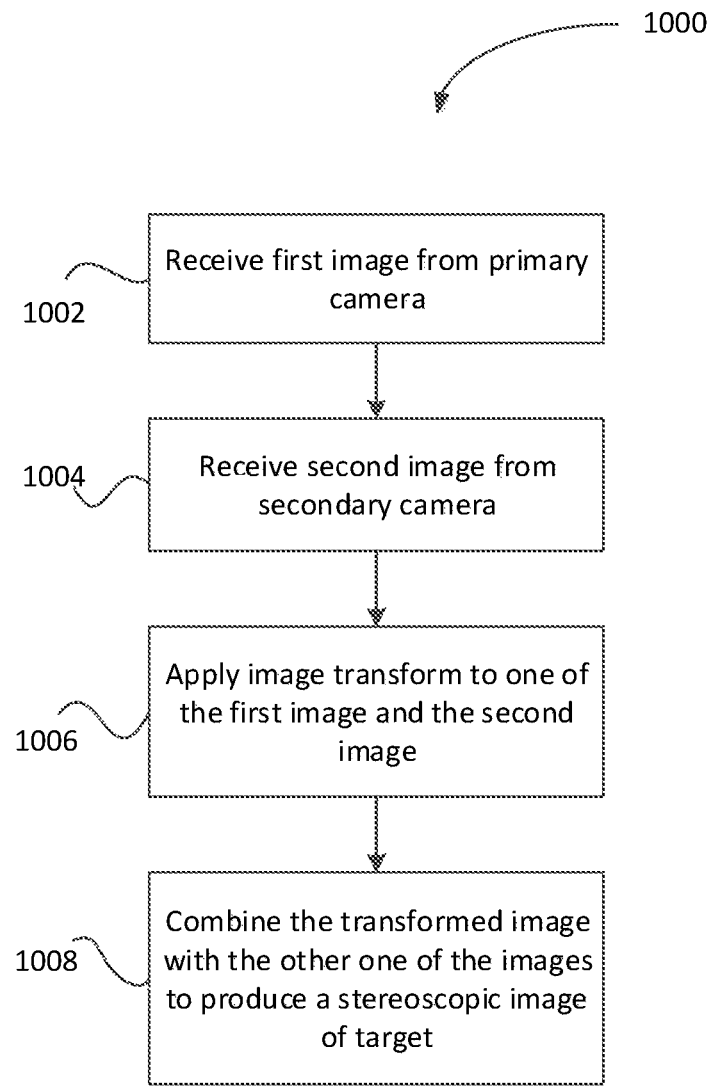
FIG. 10 is a flow diagram illustrating an example method of generating a stereoscopic image of a target, using the augmented optical imaging system, as shown in FIGS. 5A-5E.

Referring to FIG. 10, this flow diagram illustrates an example method 1000 for generating a 3D image of a target using an augmented optical imaging system, in accordance with an embodiment of the present disclosure. The method 1000 may be implemented in a digital microscope system. For example, the method 1000 may be implemented by a controller of an augmented optical imaging system integrated into a digital microscope, or similar processing unit for controlling operations of cameras of an augmented optical imaging system.

Still referring to FIG. 10, in operation 1002, the controller receives a first image from the primary camera, and in operation 1004, the controller receives a second image from the secondary camera. The controller then applies an image transform to one of the first image and the second image, in operation 1006. In at least some embodiments, the image transform is a homographic transform. In particular, the image transform implements a homograph for image rectification. With known relative camera positions, the homograph warps one of the images such that the first and second images appear as if they have been taken with only a horizontal displacement, thereby simplifying the stereo matching process in generating 3D visualization of the target. In some embodiments, the controller may be configured to determine a working distance, e.g., a stand-off distance, between the target and an aperture of the optical imaging system (or opening for the cameras' lines of sight) and determine the image transform to be applied to the one of the images based on the working distance.

Still referring to FIG. 10, the determination of the homographic transform to apply in operation 1006 may be done based on an interpolation scheme. That is, the controller may be configured to interpolate between two or more calibration homographies. Further, the controller may search a range of interpolated homographies and determine a "best" homographic transform to apply to images from the secondary camera in generating 3D visualizations. This may be done by, for example, applying each of a plurality of homographic transforms, e.g., warping, to images from the secondary camera and computing a metric that represents image correspondence between the warped images and the corresponding images from the primary camera. The controller may take, as inputs, a transform of an image from the secondary camera and a corresponding, e.g., captured substantially concurrently, image from the primary camera, and output a value for a relevant metric. A homograph that produces an optical value for the metric in question can be selected as the "best" homograph.

Still referring to FIG. 10, various different metrics may be suitably employed by the controller in the image comparisons. The metric may, for example, comprise correlation, mutual information, difference of squares, etc. The computation of the metric may be done for the entire range of interpolated homographic transforms under investigation. Depending on the metric that is used, the controller may look for either a local maximum value or a local minimum value in identifying the transform that results in highest image correspondence, or best match. For example, if a difference of squares metric is used, the controller would look for the homograph producing the lowest value for the metric from among the interpolated transforms. As another example, if image correlation is the metric used, a homograph that produces the highest value for the metric may be selected as the best homograph.

Still referring to FIG. 10, in operation 1008, the controller combines the transformed image and the other one of the images to generate a stereoscopic image of the target. In at least some embodiments, the controller may perform calibration of the zoom of the primary and secondary cameras prior to generating the stereoscopic image. For example, if the augmented optical imaging system has been moved to a significant degree or a predefined period of time has elapsed since last calibration of the cameras, the controller may be configured to automatically calibrate zoom. In some embodiments, the augmented optical imaging system may auto-calibrate for a plurality of predefined stand-off distances.

Still referring to FIG. 10 and referring back to FIGS. 4A and 5A, the navigation system 200 may be adapted to provide 3D information of a viewing target. Specifically, the navigation system 200 may incorporate a 3D visualization setup for use during a medical procedure. The 3D visualization setup may include an optical imaging system 500 that includes a primary camera, a secondary camera, and at least one optional path folding mirror. In at least some embodiments, the primary camera (which may be the optical head of the optical imaging system 500), the secondary camera, and the at least one optional path folding mirror may be housed within a single housing. The optical imaging system 500 may be connected to a positioning system 208, such as a mechanical arm or stand, which is controllable, adjustable, and moveable. The optical imaging system 500 may be mounted to the positioning system 208 such that the positioning system 208 can position and orient the optical imaging system 500.

Still referring to FIG. 10 and referring back to FIGS. 4A and 5A, operation of the optical imaging system 500 may be controlled by a processing unit of the optical imaging system 500 or the navigation system 200. The processing unit is configured to generate 3D stereoscopic images of a viewing target, based on images acquired by the primary and secondary cameras. For example, the processing unit may implement a method for generating 3D information, such as method 1000. The processing unit may also be configured to implement a calibration module for calibrating images from the cameras. The calibration module may, for example, determine a current position and orientation of the cameras of the optical imaging system 500. The calibration module may also determine transforms, e.g. homographic transforms, to apply to images of the cameras for providing 3D visualization of the viewing target.

Still referring to FIG. 10 and referring back to FIGS. 4A and 5A, the optical imaging system 500 may transmit data to the controller or to an external system, such as an external workstation. The image data acquired by the optical imaging system 500 is used to generate 3D stereoscopic images of the viewing target. The stereoscopic image information may be displayed, for example, on a 3D display device 230, e.g., 3D monitor, that is viewable using 3D glasses donned by the surgeon 201 during a procedure. The 3D information may also be useful for an augmented reality (AR) display. For example, an AR display system may use information acquired by the navigation system 200 and overlay 3D images of a target specimen on a real-time image captured by the cameras.

Figure 11:
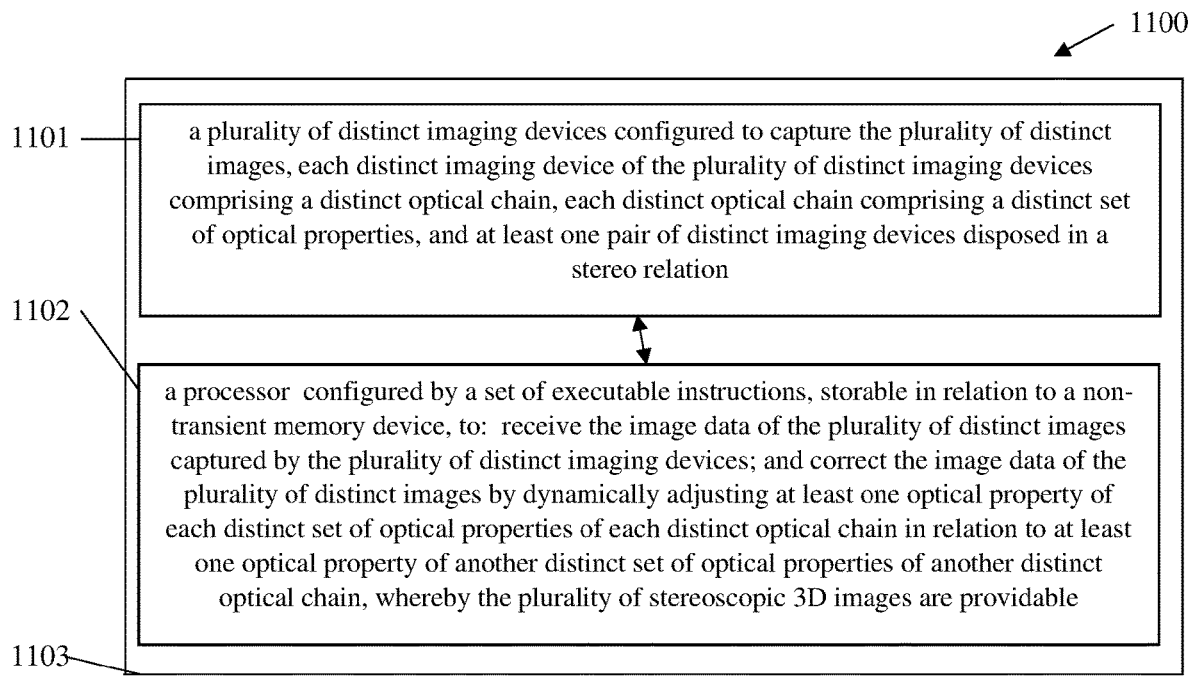
FIG. 11 is a block diagram illustrating an example system for correcting image data of a plurality of distinct images and generating a plurality of stereoscopic three-dimensional (3D) images.

Referring to FIG. 11, this block diagram illustrates an example system 1100 for correcting image data of a plurality of distinct images and generating a plurality of stereoscopic three-dimensional (3D) images, in accordance with an embodiment of the present disclosure. The system 1100 comprises: a plurality of distinct imaging devices 1101 configured to capture the plurality of distinct images, each distinct imaging device 1101 of the plurality of distinct imaging devices 1101 comprising a distinct optical chain, each distinct optical chain comprising a distinct set of optical properties, and at least one pair of distinct imaging devices 1101 disposed in a stereo relation; and a processor 1102 configured by a set of executable instructions, storable in relation to a non-transient memory device (not shown), to: receive the image data of the plurality of distinct images captured by the plurality of distinct imaging devices 1101; and correct the image data of the plurality of distinct images by dynamically adjusting at least one optical property of each distinct set of optical properties of each distinct optical chain in relation to at least one optical property of another distinct set of optical properties of another distinct optical chain, whereby the plurality of stereoscopic 3D images are providable.

Still referring to FIG. 11, the processor 1102 is further configured to correct the image data of the plurality of distinct images by using at least one of software, firmware, and hardware. The plurality of distinct imaging devices 1101 comprises a first distinct imaging device and a second distinct imaging device. The first imaging device comprises a two-dimensional (2D) imaging device; and the second imaging device comprises a fixed zoom, whereby the plurality of distinct imaging devices 1101, together, comprise a 3D imaging arrangement. The plurality of distinct imaging devices 1101 comprises a plurality of distinct optical cameras.

Still referring to FIG. 11, the processor 1102 is further configured to correct image data in relation to at least one parameter of a vertical alignment disparity, a horizontal alignment disparity, a scale disparity, and a skew disparity, among the plurality of distinct imaging devices 1101 by at least one of: dynamically digitally zooming the plurality of distinct images; and dynamically digitally warping the plurality of distinct images, whereby a series of warped homographies is generated for a plurality of distinct focal distances, and whereby a stereo zero-disparity plane is effectively digitally shifted to match the plurality of distinct focal distances.

Still referring to FIG. 11, the processor 1102 is further configured to instruct the plurality of distinct imaging devices 1101 to view a common calibration totem, wherein a plurality of matching points among the plurality of distinct imaging devices 1101 is used to determine a homographic warp of the at least one optical property of each distinct set of optical properties of each distinct optical chain in relation to the at least one optical property of another distinct set of optical properties of another distinct optical chain, whereby the plurality of distinct imaging devices 1101 are calibratable.

Still referring to FIG. 11, the processor 1102 is further configured to instruct the plurality of distinct imaging devices 1101 to view the common calibration totem (not shown) at a plurality of zoom levels and at a plurality of focal depths of a first distinct imaging device of the plurality of distinct imaging devices 1101 to generate a series of warped homographies, the plurality of intermediate zoom levels and the plurality of intermediate focal depths respectively distinct in relation to a plurality of calibrated zoom levels and a plurality of calibrated focal depths. The processor 1102 is further configured to dynamically compute a plurality of values for the plurality of intermediate zoom levels and a plurality of values for the plurality of intermediate focal depths by respectively interpolating between each value of the calibrated zoom level of the plurality of calibrated zoom levels and each value of the calibrated focal depth of the plurality of calibrated focal depths.

Figure 12:
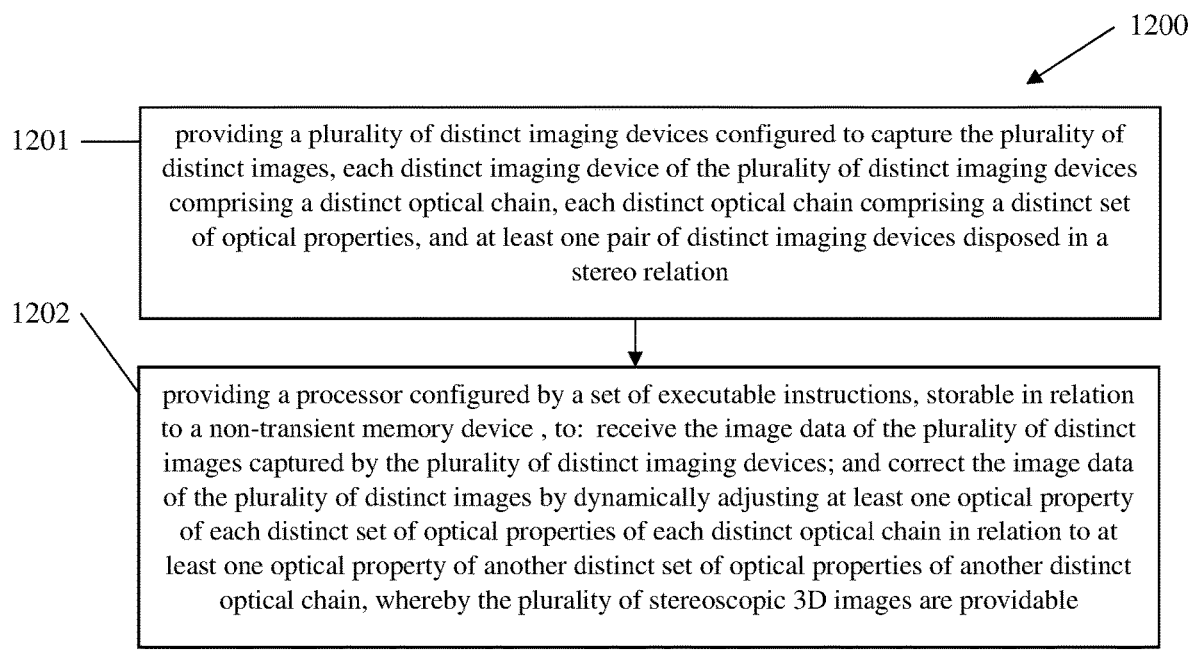
FIG. 12 is a flow diagram illustrating a method of providing a system for correcting image data of a plurality of distinct images and generating a plurality of stereoscopic three-dimensional (3D) images.

Referring to FIG. 12, this flow diagram illustrates a method 1200 of providing a system 1100 for correcting image data of a plurality of distinct images and generating plurality of stereoscopic three-dimensional (3D) images, in accordance with an embodiment of the present disclosure. The method 1200 comprises: providing a plurality of distinct imaging devices 1101 configured to capture the plurality of distinct images, each distinct imaging device 1101 of the plurality of distinct imaging devices 1101 comprising a distinct optical chain, each distinct optical chain comprising a distinct set of optical properties, and at least one pair of distinct imaging devices 1101 disposed in a stereo relation, as indicated by block 1201; and providing a processor 1102 configured by a set of executable instructions, storable in relation to a non-transient memory device (not shown), to: receive the image data of the plurality of distinct images captured by the plurality of distinct imaging devices 1101; and correct the image data of the plurality of distinct images by dynamically adjusting at least one optical property of each distinct set of optical properties of each distinct optical chain in relation to at least one optical property of another distinct set of optical properties of another distinct optical chain, as indicated by block 1202, whereby the plurality of stereoscopic 3D images are providable.

Still referring to FIG. 12, providing the processor is further configuring the processor 1102 to correct the image data of the plurality of distinct images by using at least one of software, firmware, and hardware. Providing the plurality of distinct imaging devices 1101 comprises providing a first distinct imaging device and providing a second distinct imaging device. Providing the first distinct imaging device comprises providing a two-dimensional (2D) imaging device; and providing the second distinct imaging device comprises providing the second distinct imaging device with a fixed zoom, and whereby the plurality of distinct imaging devices 1101, together, comprise a 3D imaging arrangement. Providing the plurality of distinct imaging devices 1101 comprises providing a plurality of distinct optical cameras.

Still referring to FIG. 12, providing the processor 1102 further comprises configuring the processor 1102 to correct image data in relation to at least one parameter of a vertical alignment disparity, a horizontal alignment disparity, a scale disparity, and a skew disparity, among the plurality of distinct imaging devices 1101 by at least one of: dynamically digitally zooming the plurality of distinct images; and dynamically digitally warping the plurality of distinct images, whereby a series of warped homographies is generated for a plurality of distinct focal distances, and whereby a stereo zero-disparity plane is effectively digitally shifted to match the plurality of distinct focal distances.

Still referring to FIG. 12, providing the processor 1102 comprises further configuring the processor 1102 to instruct the plurality of distinct imaging devices 1101 to view a common calibration totem (not shown), wherein a plurality of matching points among the plurality of distinct imaging devices 1101 is used to determine a homographic warp of the at least one optical property of each distinct set of optical properties of each distinct optical chain in relation to the at least one optical property of another distinct set of optical properties of another distinct optical chain, whereby the plurality of distinct imaging devices 1101 are calibratable.

Still referring to FIG. 12, providing the processor 1102 comprises further configuring the processor 1102 to instruct the plurality of distinct imaging devices 1101 to view the common calibration totem (not shown) at a plurality of zoom levels and at a plurality of focal depths of a first distinct imaging device 1101*a* of the plurality of distinct imaging devices 1101 to generate a series of warped homographies, the plurality of intermediate zoom levels and the plurality of intermediate focal depths respectively distinct in relation to a plurality of calibrated zoom levels and a plurality of calibrated focal depths. Providing the processor 1102 comprises further configuring the processor 1102 to dynamically compute a plurality of values for the plurality of intermediate zoom levels and a plurality of values for the plurality of intermediate focal depths by respectively interpolating between each value of the calibrated zoom level of the plurality of calibrated zoom levels and each value of the calibrated focal depth of the plurality of calibrated focal depths. Specifically, the homography is interpolated between the calibrated homographies of the nearest calibration zoom values and focus values.

Figure 13:
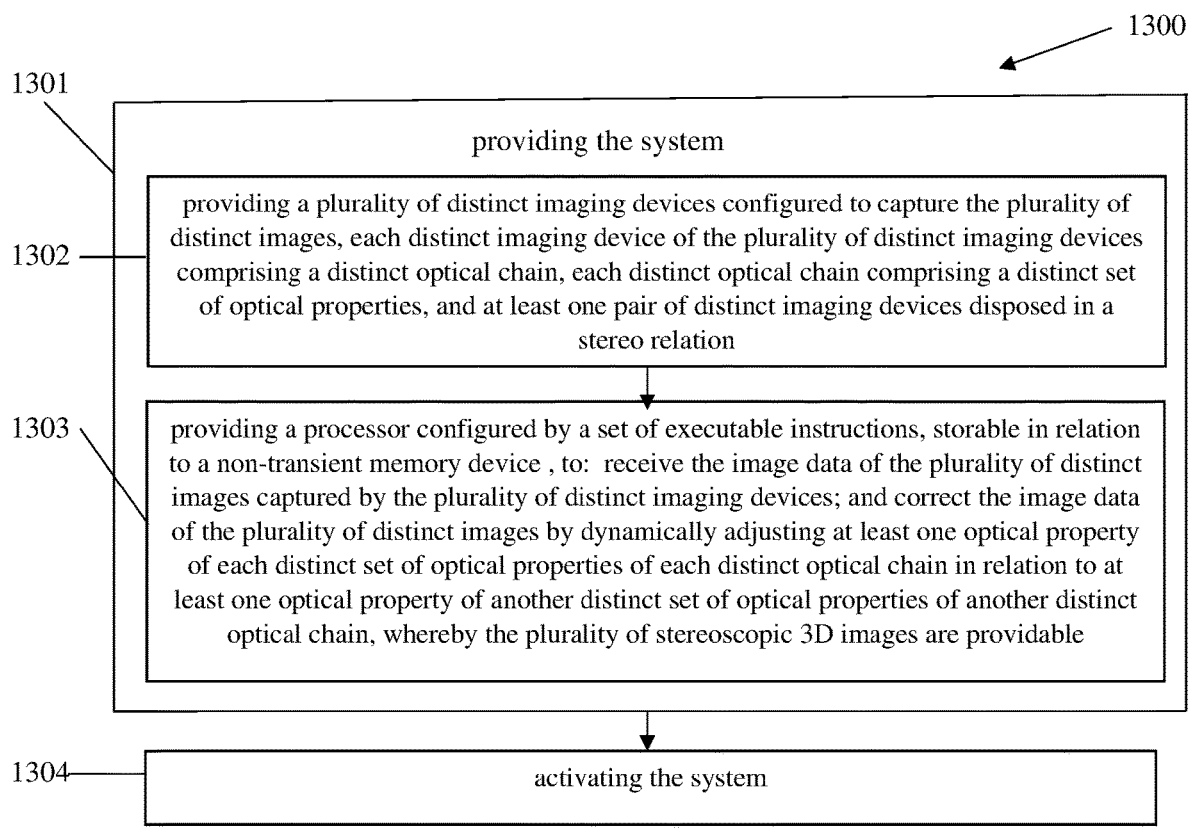
FIG. 13 is a flow diagram illustrating a method of correcting image data of a plurality of distinct images and generating a plurality of stereoscopic three-dimensional (3D) images by way of a system.

Referring to FIG. 13, this flow diagram illustrates a method 1300 of generating and correcting a plurality of images by way of a system 1100, in accordance with am embodiment of the present disclosure. The method 1300 comprises: providing the system 1100, as indicated by block 1301, providing the system 1100 comprising: providing a plurality of distinct imaging devices 1101 configured to capture the plurality of distinct images, each distinct imaging device 1101 of the plurality of distinct imaging devices 1101 comprising a distinct optical chain, each distinct optical chain comprising a distinct set of optical properties, and at least one pair of distinct imaging devices 1101 disposed in a stereo relation, as indicated by block 1302; and providing a processor 1102 configured by a set of executable instructions, storable in relation to a non-transient memory device (not shown), to: receive the image data of the plurality of distinct images captured by the plurality of distinct imaging devices 1101; and correct the image data of the plurality of distinct images by dynamically adjusting at least one optical property of each distinct set of optical properties of each distinct optical chain in relation to at least one optical property of another distinct set of optical properties of another distinct optical chain, whereby the plurality of stereoscopic 3D images are providable, as indicated by block 1303; and activating the system, as indicated by block 1304, thereby generating and correcting at least one stereoscopic three-dimensional (3D) image.

Referring back to FIGS. 11-13, in some embodiments, a method of providing a stereo (3D) viewing system involves adding an independent secondary camera to a 2D system, e.g., retrofitting a pre-existing 2D system. The independent secondary camera has a fixed zoom and optical properties that are distinct in relation to the zoom and optical properties of a primary camera. The difference between the cameras is corrected through software, by way of digitally zooming and warping the secondary image to match the primary image. This is accomplished through a one-time calibration process which involves having both cameras view a common calibration totem. This produces matching correspondence points between the two cameras which is used to determine a homographic warp of the left camera to match the optical properties of the right camera. This calibration can be done at a number of zooms and focal depths of the primary camera to produce a series of warp homographies. Further, homographies at intermediate zooms and focal depths, e.g., ones that do not correspond to the calibrated zoom and focal depths,) can be computed dynamically by interpolating between the nearest calibrated homographies. Alternatively, the secondary camera has an adjustable zoom and optical properties that are distinct in relation to the zoom and optical properties of a primary camera. Additionally, if the calibration homographies record the generating zoom levels and focus levels of both the primary camera and the secondary camera, the system can compute a homography to adjust the secondary camera to the primary camera for any input, e.g., any available input.

Still referring back to FIGS. 11-13, the system 1100 can correct for vertical alignment disparities between the left and right cameras by way of warping. The system also generates different warping homographies for different focal distances, thereby effectively shifting the stereo zero-disparity plane to match the different focal distances. In the related art, this technique is very difficult to mechanically perform since changing the zero-disparity distance mechanically involves changing the toe-in angle between the two cameras such that their optical axes intersect at the desired depth. This also means that the method has utility in matched optics systems as well, thereby correcting for slight alignment inaccuracies and allowing dynamic adjustment of the zero-disparity plane.

Information, as herein shown and described in detail, is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

What is claimed:

1. A system for correcting image data of a plurality of distinct images and generating a plurality of stereoscopic three-dimensional (3D) images, the system comprising:
  a plurality of distinct imaging devices configured to capture the plurality of distinct images, each distinct imaging device of the plurality of distinct imaging devices comprising a distinct optical chain, each distinct optical chain comprising a distinct set of optical properties, and at least one pair of distinct imaging devices disposed in a stereo relation; and a processor configured by a set of executable instructions, storable in relation to a non-transient memory device, to:

receive the image data of the plurality of distinct images captured by the plurality of distinct imaging devices; and correct the image data of the plurality of distinct images by dynamically adjusting at least one optical property of each distinct set of optical properties of each distinct optical chain in relation to at least one optical property of another distinct set of optical properties of another distinct optical chain, whereby the plurality of stereoscopic 3D images are providable;

wherein the processor is further configured to correct the image data in relation to at least one parameter of a vertical alignment disparity, a horizontal alignment disparity, a scale disparity, and a skew disparity, among the plurality of distinct imaging devices by at least one of: dynamically digitally zooming the plurality of distinct images; and dynamically digitally warping the plurality of distinct images, whereby a series of warped homographies is generated for a plurality of distinct focal distances, and whereby a stereo zero-disparity plane is effectively digitally shifted to match the plurality of distinct focal distances.

2. The system of claim 1, wherein the processor is further configured to correct the image data of the plurality of distinct images by using at least one of software, firmware, and hardware.

3. The system of claim 1, wherein the plurality of distinct imaging devices comprises a first distinct imaging device and a second imaging device, wherein the first distinct imaging device comprises a two-dimensional (2D) imaging device, and wherein the second distinct imaging device comprises a fixed lens providing a fixed zoom, and whereby the plurality of distinct imaging devices, together, comprise a 3D imaging arrangement.

4. The system of claim 1, wherein the plurality of distinct imaging devices comprises a plurality of distinct optical cameras.

5. The system of claim 1, wherein the processor is further configured to instruct the plurality of distinct imaging devices to view a common calibration totem, wherein a plurality of matching points among the plurality of distinct imaging devices is used to determine a homographic warp of the at least one optical property of each distinct set of optical properties of each distinct optical chain in relation to the at least one optical property of another distinct set of optical properties of another distinct optical chain, whereby the plurality of distinct imaging devices are calibratable.

6. The system of claim 5, wherein the processor is further configured to instruct the plurality of distinct imaging devices to view the common calibration totem at a plurality of zoom levels and at a plurality of focal depths of the first distinct imaging device of the plurality of distinct imaging devices to generate the series of warped homographies.

7. The system of claim 6, wherein the processor is further configured to generate calibrations at a plurality of zoom settings for the secondary camera.

8. The system of claim 7, wherein the processor is further configured to dynamically compute a plurality of values for a plurality of intermediate zoom levels and a plurality of values for a plurality of intermediate focal depths by respectively interpolating between each value of the calibrated zoom level of the plurality of calibrated zoom levels and each value of the calibrated focal depth of the plurality of calibrated focal depths.

9. The system of claim 1, wherein the processor is further configured to correct the image data of the plurality of distinct images by using at least one of software, firmware, and hardware, wherein the plurality of distinct imaging devices comprises the first distinct imaging device and the second distinct imaging device, wherein the first distinct imaging device comprises a two-dimensional (2D) imaging device, wherein the second distinct imaging device comprises a fixed zoom, whereby the plurality of distinct imaging devices, together, comprise a 3D imaging arrangement, wherein the plurality of distinct imaging devices comprises the plurality of distinct optical cameras, wherein the processor is further configured to correct the image data in relation to at least one parameter of a vertical alignment disparity, a horizontal alignment disparity, a scale disparity, and a skew disparity, among the plurality of distinct imaging devices by at least one of: dynamically digitally zooming the plurality of distinct images; and dynamically digitally warping the plurality of distinct images, whereby the series of warped homographies is generated for a plurality of distinct focal distances, and whereby a stereo zero-disparity plane is effectively digitally shifted to match the plurality of distinct focal distances, wherein the processor is further configured to instruct the plurality of distinct imaging devices to view a common calibration totem, wherein a plurality of matching points among the plurality of distinct imaging devices is used to determine a homographic warp of the at least one optical property of each distinct set of optical properties of each distinct optical chain in relation to the at least one optical property of another distinct set of optical properties of another distinct optical chain, whereby the plurality of distinct imaging devices are calibratable, wherein the processor is further configured to instruct the plurality of distinct imaging devices to view the common calibration totem at a plurality of zoom levels and at a plurality of focal depths of the first distinct imaging device of the plurality of distinct imaging devices to generate the series of warped homographies, the plurality of intermediate zoom levels and the plurality of intermediate focal depths respectively distinct in relation to a plurality of calibrated zoom levels and a plurality of calibrated focal depths, and wherein the processor is further configured to dynamically compute a plurality of values for the plurality of intermediate zoom levels and a plurality of values for the plurality of intermediate focal depths by respectively interpolating between each value of the calibrated zoom level of the plurality of calibrated zoom levels and each value of the calibrated focal depth of the plurality of calibrated focal depths.

10. A method of providing a system for correcting image data of a plurality of distinct images and generating plurality of stereoscopic three-dimensional (3D) images, the method comprising:

providing a plurality of distinct imaging devices configured to capture the plurality of distinct images, each distinct imaging device of the plurality of distinct imaging devices comprising a distinct optical chain, each distinct optical chain comprising a distinct set of optical properties, and at least one pair of distinct imaging devices disposed in a stereo relation; and providing a processor configured by a set of executable instructions, storable in relation to a non-transient memory device, to:

receive the image data of the plurality of distinct images captured by the plurality of distinct imaging devices; and correct the image data of the plurality of distinct images by dynamically adjusting at least one optical property of each distinct set of optical properties of each distinct optical chain in relation to at least one optical property of another distinct set of optical properties of another distinct optical chain, whereby the plurality of stereoscopic 3D images are providable;

wherein providing the processor further comprises configuring the processor to correct the image data in relation to at least one parameter of a vertical alignment disparity, a horizontal alignment disparity, a scale disparity, and a skew disparity, among the plurality of distinct imaging devices by at least one of: dynamically digitally zooming the plurality of distinct images; and dynamically digitally warping the plurality of distinct images, whereby a series of warped homographies is generated for a plurality of distinct focal distances, and whereby a stereo zero-disparity plane is effectively digitally shifted to match the plurality of distinct focal distances.

11. The method of claim 10, wherein providing the processor is further configuring the processor to correct the image data of the plurality of distinct images by using at least one of software, firmware, and hardware.

12. The method of claim 10, wherein providing the plurality of distinct imaging devices comprises providing a first distinct imaging device and providing a second distinct imaging device, wherein providing the first distinct imaging device comprises providing a two-dimensional (2D) imaging device, and wherein providing the second distinct imaging device comprises providing the second distinct imaging device with a fixed lens providing a fixed zoom, and whereby the plurality of distinct imaging devices, together, comprise a 3D imaging arrangement.

13. The method of claim 10, wherein providing the plurality of distinct imaging devices comprises providing a plurality of distinct optical cameras.

14. The method of claim 10, wherein providing the processor comprises further configuring the processor to instruct the plurality of distinct imaging devices to view a common calibration totem, wherein a plurality of matching points among the plurality of distinct imaging devices is used to determine a homographic warp of the at least one optical property of each distinct set of optical properties of each distinct optical chain in relation to the at least one optical property of another distinct set of optical properties of another distinct optical chain, whereby the plurality of distinct imaging devices are calibratable.

15. The method of claim 14, wherein providing the processor comprises further configuring the processor to instruct the plurality of distinct imaging devices to view the common calibration totem at a plurality of zoom levels and at a plurality of focal depths of the first distinct imaging device of the plurality of distinct imaging devices to generate the series of warped homographies.

16. The method of claim 15,
wherein providing the processor comprises further configuring the processor to generate calibrations at a plurality of zoom settings for the secondary camera, and wherein providing the processor comprises further configuring the processor to dynamically compute a plurality of values for a plurality of intermediate zoom levels and a plurality of values for a plurality of intermediate focal depths by respectively interpolating between each value of the calibrated zoom level of the plurality of calibrated zoom levels and each value of the calibrated focal depth of the plurality of calibrated focal depths.

17. The method of claim 10,
wherein providing the processor is further configuring the processor to correct the image data of the plurality of distinct images by using at least one of software, firmware, and hardware, wherein providing the plurality of distinct imaging devices comprises providing a first imaging device and providing a second imaging device, wherein providing the first imaging device comprises providing a two-dimensional (2D) imaging device, wherein providing the second imaging device comprises providing the second imaging device with a fixed zoom, whereby the plurality of distinct imaging devices, together, comprise a 3D imaging arrangement, wherein providing the plurality of distinct imaging devices comprises providing the plurality of distinct optical cameras, wherein providing the processor further comprises configuring the processor to correct the image data in relation to at least one parameter of a vertical alignment disparity, a horizontal alignment disparity, a scale disparity, and a skew disparity, among the plurality of distinct imaging devices by at least one of: dynamically digitally zooming the plurality of distinct images; and dynamically digitally warping the plurality of distinct images, whereby the series of warped homographies is generated for a plurality of distinct focal distances, and whereby a stereo zero-disparity plane is effectively digitally shifted to match the plurality of distinct focal distances, wherein providing the processor comprises further configuring the processor to instruct the plurality of distinct imaging devices to view a common calibration totem, wherein a plurality of matching points among the plurality of distinct imaging devices is used to determine a homographic warp of the at least one optical property of each distinct set of optical properties of each distinct optical chain in relation to the at least one optical property of another distinct set of optical properties of another distinct optical chain, whereby the plurality of distinct imaging devices are calibrated, wherein providing the processor comprises further configuring the processor to instruct the plurality of distinct imaging devices to view the common calibration totem at a plurality of zoom levels and at a plurality of focal depths of the first distinct imaging device of the plurality of distinct imaging devices to generate the series of warped homographies, and the plurality of intermediate zoom levels and the plurality of intermediate focal depths respectively distinct in relation to a plurality of calibrated zoom levels and a plurality of calibrated focal depths, and wherein providing the processor comprises further configuring the processor to dynamically compute a plurality of values for the plurality of intermediate zoom levels and a plurality of values for the plurality of intermediate focal depths by respectively interpolating between each value of the calibrated zoom level of the plurality of calibrated zoom levels and each value of the calibrated focal depth of the plurality of calibrated focal depths.

18. A method of correcting image data of a plurality of distinct images and generating plurality of stereoscopic three-dimensional (3D) images by way of a system, the method comprising:

providing the system, providing the system comprising:
providing a plurality of distinct imaging devices configured to capture the plurality of distinct images, each distinct imaging device of the plurality of distinct imaging devices comprising a distinct optical chain, each distinct optical chain comprising a distinct set of optical properties, and at least one pair of distinct imaging devices disposed in a stereo relation; and
providing a processor configured by a set of executable instructions, storable in relation to a non-transient memory device, to: receive the image data of the plurality of distinct images captured by the plurality of distinct imaging devices; and correct the image data of the plurality of distinct images by dynamically adjusting at least one optical property of each distinct set of optical properties of each distinct optical chain in relation to at least one optical property of another distinct set of optical properties of another distinct optical chain, whereby the plurality of stereoscopic 3D images are providable; and activating the system, thereby generating and correcting at least one stereoscopic three-dimensional (3D) image;

wherein the processor is further configured to correct the image data in relation to at least one parameter of a vertical alignment disparity, a horizontal alignment disparity, a scale disparity, and a skew disparity, among the plurality of distinct imaging devices by at least one of: dynamically digitally zooming the plurality of distinct images; and dynamically digitally warping the plurality of distinct images, whereby a series of warped homographies is generated for a plurality of distinct focal distances, and whereby a stereo zero-disparity plane is effectively digitally shifted to match the plurality of distinct focal distances.

* * * * *